(12) United States Patent
Boyer, II et al.

(10) Patent No.: US 7,014,659 B2
(45) Date of Patent: Mar. 21, 2006

(54) SKELETAL RECONSTRUCTION CAGES

(75) Inventors: Michael L. Boyer, II, Paoli, PA (US);
David C. Paul, Phoenixville, PA (US);
Thomas B. Higgins, Berwyn, PA (US);
Christopher M. Angelucci,
Schwenksville, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 10/730,011

(22) Filed: Dec. 9, 2003

(65) Prior Publication Data

US 2004/0181283 A1 Sep. 16, 2004

Related U.S. Application Data

(62) Division of application No. 09/814,215, filed on Mar. 22, 2001, now Pat. No. 6,660,038.

(60) Provisional application No. 60/191,099, filed on Mar. 22, 2000.

(51) Int. Cl.
*A61F 2/44* (2006.01)
(52) U.S. Cl. .................. 623/17.15; 623/17.11
(58) Field of Classification Search .. 623/17.11–17.16, 623/11.11
See application file for complete search history.

(56) References Cited

U.S. PATENT DOCUMENTS

| | | |
|---|---|---|
| 4,501,269 A | 2/1985 | Bagby |
| 4,820,305 A | 4/1989 | Harms et al. |
| 4,834,757 A | 5/1989 | Brantigan |
| 4,950,296 A | 8/1990 | McIntyre |
| 4,961,740 A | 10/1990 | Ray et al. |
| 5,015,247 A | 5/1991 | Michelson |
| 5,026,373 A | 6/1991 | Ray et al. |
| 5,055,104 A | 10/1991 | Ray |
| 5,062,850 A | 11/1991 | MacMillan et al. |
| 5,147,404 A | 9/1992 | Downey |
| 5,192,327 A | 3/1993 | Brantigan |
| 5,211,664 A | 5/1993 | Tepic et al. |
| 5,281,226 A | 1/1994 | Davydov et al. |
| 5,284,655 A | 2/1994 | Bogdansky et al. |
| 5,314,476 A | 5/1994 | Prewett et al. |
| 5,405,391 A | 4/1995 | Hednerson et al. |
| 5,423,817 A | 6/1995 | Lin |
| 5,439,684 A | 8/1995 | Prewett et al. |
| 5,458,638 A | 10/1995 | Kuslich et al. |
| 5,489,308 A | 2/1996 | Kuslich et al. |
| 5,507,818 A | 4/1996 | McLaughlin |
| 5,514,180 A | 5/1996 | Heggeness et al. |

(Continued)

FOREIGN PATENT DOCUMENTS

DE 44 09 392 A1 9/1995

(Continued)

OTHER PUBLICATIONS

Fred H. Albee, *Bone Graft Surgery in Disease, Injury and Deformity*, D. Appleton-Century Company, Inc., New York, 1940, pp. 30, 114, 151, 155, 164, 212, 256-257, 311-313.

(Continued)

*Primary Examiner*—Pedro Philogene
(74) *Attorney, Agent, or Firm*—Jones Day

(57) ABSTRACT

Skeletal reconstruction cages include a central body having first and second ends, a first end cap coupled to one end of the central body, and a second end cap coupled to the other end of the central body. At least two of the central body, first end cap, and second end cap are formed from bone. Each of the central body, first end cap, and second end cap may be provided in different sizes so that cages with varying overall heights, and related angulations, may be created.

25 Claims, 13 Drawing Sheets

U.S. PATENT DOCUMENTS

| | | |
|---|---|---|
| 5,522,899 A | 6/1996 | Michelson |
| 5,534,029 A | 7/1996 | Shima |
| 5,534,030 A | 7/1996 | Navarro et al. |
| 5,549,679 A | 8/1996 | Kuslich |
| 5,554,191 A | 9/1996 | Lahille et al. |
| 5,571,190 A | 11/1996 | Ulrich et al. |
| 5,571,192 A | 11/1996 | Schönhöffer |
| 5,609,635 A | 3/1997 | Michelson |
| 5,609,636 A | 3/1997 | Kohrs et al. |
| 5,609,637 A | 3/1997 | Biedermann et al. |
| 5,674,295 A | 10/1997 | Ray et al. |
| 5,683,394 A | 11/1997 | Rinner |
| 5,683,463 A | 11/1997 | Godefroy et al. |
| 5,683,464 A | 11/1997 | Wagner et al. |
| 5,700,291 A | 12/1997 | Kuslich et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,755,798 A | 5/1998 | Papavero et al. |
| 5,766,253 A | 6/1998 | Brosnahan, III |
| 5,776,197 A | 7/1998 | Rabbe et al. |
| 5,776,198 A | 7/1998 | Rabbe et al. |
| 5,776,199 A | 7/1998 | Michelson |
| 5,785,710 A | 7/1998 | Michelson |
| D397,439 S | 8/1998 | Koros et al. |
| 5,800,547 A | 9/1998 | Schäfer et al. |
| 5,827,328 A | 10/1998 | Buttermann |
| D403,069 S | 12/1998 | Drewry et al. |
| 5,860,973 A | 1/1999 | Michelson |
| 5,861,041 A | 1/1999 | Tienboon |
| 5,865,845 A | 2/1999 | Thalgott |
| 5,865,848 A | 2/1999 | Baker |
| 5,885,299 A | 3/1999 | Winslow et al. |
| 5,888,222 A | 3/1999 | Coates et al. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,904,719 A | 5/1999 | Errico et al. |
| 5,910,315 A | 6/1999 | Stevenson et al. |
| 5,968,098 A | 10/1999 | Winslow |
| 5,972,031 A | 10/1999 | Biedermann et al. |
| 5,972,368 A | 10/1999 | McKay |
| 5,976,187 A | 11/1999 | Richelsoph |
| 5,980,522 A | 11/1999 | Koros et al. |
| 5,984,967 A | 11/1999 | Zdeblick et al. |
| 5,989,289 A | 11/1999 | Coates et al. |
| 5,989,290 A | 11/1999 | Biedermann et al. |
| 6,015,436 A | 1/2000 | Schönhöffer |
| 6,025,538 A | 2/2000 | Yaccarino, III |
| 6,033,405 A | 3/2000 | Winslow et al. |
| 6,045,579 A | 4/2000 | Hochshuler et al. |
| 6,045,580 A | 4/2000 | Scarborough et al. |
| 6,063,121 A | 5/2000 | Xavier et al. |
| 6,080,158 A | 6/2000 | Lin |
| 6,080,193 A | 6/2000 | Hochshuler et al. |
| 6,086,613 A | 7/2000 | Camino et al. |
| 6,126,689 A | 10/2000 | Brett |
| 6,129,763 A | 10/2000 | Chauvin et al. |
| 6,136,031 A | 10/2000 | Middleton |
| 6,143,033 A | 11/2000 | Paul et al. |
| 6,149,686 A | 11/2000 | Kuslich et al. |
| 6,176,882 B1 | 1/2001 | Biedermann et al. |
| 6,193,756 B1 | 2/2001 | Studer et al. |
| 6,200,347 B1 | 3/2001 | Anderson et al. |
| 6,241,769 B1 | 6/2001 | Nicholson et al. |
| 6,245,108 B1 | 6/2001 | Biscup |
| 6,258,125 B1 | 7/2001 | Paul et al. |
| 6,458,158 B1 | 10/2002 | Anderson et al. |
| 2001/0001129 A1 | 5/2001 | McKay et al. |
| 2001/0010021 A1 | 7/2001 | Boyd et al. |
| 2001/0016777 A1 | 8/2001 | Biscup |
| 2002/0106393 A1 | 8/2002 | Bianchi et al. |

FOREIGN PATENT DOCUMENTS

| | | |
|---|---|---|
| DE | 195 09 317 A1 | 9/1996 |
| DE | 44 23 257 A1 | 11/1996 |
| DE | 195 04 867 C1 | 12/1997 |
| EP | 0 577 178 A1 | 1/1994 |
| EP | 0 639 351 A2 | 11/1996 |
| EP | 0 832 622 A2 | 4/1998 |
| EP | 0 966 930 | 12/1999 |
| EP | 0 968 692 A1 | 1/2000 |
| FR | 2 700 947 | 8/1994 |
| FR | 2 697 996 | 9/1995 |
| FR | 2 753 368 | 10/2000 |
| RU | 2008851 C1 | 3/1994 |
| WO | WO 92/01428 | 2/1992 |
| WO | WO 96/37170 | 11/1996 |
| WO | WO 96/39988 | 12/1996 |
| WO | WO 97/20526 | 6/1997 |
| WO | WO 98/17209 | 4/1998 |
| WO | WO 98/29047 | 7/1998 |
| WO | WO 98/55052 | 12/1998 |
| WO | WO 99/32055 | 7/1999 |
| WO | WO 99/38461 | 8/1999 |
| WO | WO 99/56675 | 11/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/74607 A1 | 12/2000 |

OTHER PUBLICATIONS

Fred H. Albee, "Bone Surgery With Machine Tools," *Scientific American*, Apr., 1936, pp. 178-181.

Fred H. Albee, *Bone-Graft Surgery*, W. B. Saunders Company, Philadelphia, Pennsylvania, 1915, pp. 145, 165-166, 171, 368-369.

SynMesh System Technique Guide, Synthes Spine, Dec., 2002.

SKELETAL RECONSTRUCTION CAGES

CROSS-REFERENCE TO RELATED APPLICATIONS

This application is a divisional of prior patent application Ser. No. 09/814,215, filed Mar. 22, 2001, now U.S. Pat. No. 6,660,038, which in turn claims the benefit of Provisional Application No. 60/191,099 filed Mar. 22, 2000 under 35 U.S.C. § 119(e). The entire contents of these applications are expressly incorporated herein by reference thereto.

FIELD OF THE INVENTION

The invention relates to an implant for orthopedic applications. More particularly, the invention is related to skeletal reconstruction cages formed from bone for filling vacancies in bone tissue.

BACKGROUND OF THE INVENTION

Bone grafts have become an important and accepted means for treating bone fractures and defects. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. This is primarily due to the limited applicability of xenografts, transplants from another species.

Orthopedic autografts or autogenous grafts involve source bone acquired from the same individual that will receive the transplantation. Thus, this type of transplant moves bony material from one location in a body to another location in the same body, and has the advantage of producing minimal immunological complications. It is not always possible or even desirable to use an autograft. The acquisition of bone material from the body of a patient typically requires a separate operation from the implantation procedure. Furthermore, the removal of material, oftentimes involving the use of healthy material from the pelvic area or ribs, has the tendency to result in additional patient discomfort during rehabilitation, particularly at the location of the material removal. Grafts formed from synthetic material have also been developed, but the difficulty in mimicking the properties of bone limits the efficacy of these implants.

As a result of the challenges posed by autografts and synthetic grafts, many orthopedic procedures alternatively involve the use of allografts, which are bone grafts from other human sources (normally cadavers). The bone grafts, for example, are placed in a host bone and serve as the substructure for supporting new bone tissue growth from the host bone. The grafts are sculpted to assume a shape that is appropriate for insertion at the fracture or defect area, and often require fixation to that area as by screws or pins. Due to the availability of allograft source material, and the widespread acceptance of this material in the medical community, the use of allograft tissues is certain to expand in the field of musculoskeletal surgery.

Various spinal conditions are managed, in part, by the introduction of bone grafts. For example, degeneration in the intervertebral discs of the cervical spine and the points between the vertebrae can result in abnormal pressure on the spinal cord that must be relieved with surgical intervention. It is known to ease undesirable pressure by surgically removing the degenerated tissue, such as the vertebrae, and replacing the surgically-created void with a bone graft. Other reasons for surgical removal of spinal tissue include disease such as cancer or other trauma. The procedure of removing vertebral bodies and the discs between each vertebra is known as a corpectomy, i.e., a removal of the body. A bone autograft suitable for this purpose is often taken from a patient's pelvis or leg bones. Typically, the graft is in the form of a strut or block of bone, which is shaped to fit into adjoining vertebral bodies to fill the empty space and maintain proper spacing between remaining vertebrae. The strut also preserves proper anatomic orientation, while promoting bony fusion with surroundings for subsequent stability.

Fusion procedures may be performed in the cervical, thoracic or lumbar spine, and following placement of the bone graft, a unicortical locking plate is typically installed over the graft by screwing it into the adjoining vertebral bodies. The plate may enhance stability until bony fusion occurs, as well as prevent dislodgment of the graft.

The frequency of corpectomies has created a demand for improved implant designs as well as novel approaches to forming the implants, such as with allografts. In order to provide such implants, an understanding of the sources of allograft bone and the characteristics of bone is useful.

Different bones of the body such as the femur (thigh), tibia and fibula (leg), humerus (upper arm), radius and ulna (lower arm) have geometries that vary considerably. In addition, the lengths of these bones vary; for example, in an adult the lengths may vary from 47 centimeters (femur) to 26 centimeters (radius). Furthermore, the shape of the cross section of each type of bone varies considerably, as does the shape of any given bone over its length. While a femur has a generally rounded outer shape, a tibia has a generally triangular outer shape. Also, the wall thickness varies in different areas of the cross-section of each bone. Thus, the use of any given bone to produce an implant component may be a unction of the bone's dimensions and geometry. Machining of bones, however, may permit the production of implant components with standardized dimensions.

As a collagen-rich and mineralized tissue, bone is composed of about forty percent organic material (mainly collagen), with the remainder being inorganic material (mainly a near-hydroxyapatite composition resembling $3Ca_3(PO_4)_2 \cdot Ca(OH)_2$). Structurally, the collagen assumes a fibril formation, with hydroxyapatite crystals disposed along the length of the fibril, and the individual fibrils are disposed parallel to each other forming fibers. Depending on the type of bone, the fibrils are either interwoven, or arranged in lamellae that are disposed perpendicular to each other.

There is little doubt that bone tissues have a complex design, and there are substantial variations in the properties of bone tissues with respect to the type of bone (i.e., leg, arm, vertebra) as well as the overall structure of each type. For example, when tested in the longitudinal direction, leg and arm bones have a modulus of elasticity of about 17 to 19 GPa, while vertebra tissue has a modulus of elasticity of less than 1 GPa. The tensile strength of leg and arm bones varies between about 120 MPa and about 150 MPa, while vertebra have a tensile strength of less than 4 MPa. Notably, the compressive strength of bone varies, with the femur and humerus each having a maximum compressive strength of about 167 MPa and 132 MPa respectively. Again, the vertebra have a far lower compressive strength of no more than about 10 MPa.

With respect to the overall structure of a given bone, the mechanical properties vary throughout the bone. For example, a long bone (leg bone) such as the femur has both compact bone and spongy bone. Cortical bone, the compact and dense bone that surrounds the marrow cavity, is generally solid and thus carries the majority of the load in major bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10–20 MPa and a density of about 0.7, cortical bone has a tensile strength of about 100–200 MPa and a density of about 2. Additionally, the strain to failure of cancellous bone is about 5–7%, while cortical bone can only withstand 1–3% strain before failure. It should also be noted that these mechanical characteristics may degrade as a result of numerous factors such as any chemical treatment applied to the bone material, and the manner of storage after removal but prior to implantation (i.e. drying of the bone).

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. Thus, the design of an implant using cancellous bone may be tailored to specifically incorporate material of a desired porosity.

It is essential to recognize the distinctions in the types and properties of bones when considering the design of implants. Surgeons often work with bones using similar tools as would be found in carpentry, adapted for use in the operating room environment. This suggests that bones have some properties which are similar to some types of wood, for example ease in sawing and drilling. Notably, however, are many differences from wood such as the abrasive nature of hydroxyapatite and the poor response to local heating during machining of a bone. The combination of tensile and compressive strengths found in bone, resulting from the properties of the collagen and hydroxyapatite, is thus more aptly compared to the high tensile and compressive strengths found in reinforced concrete, due to steel and cement. Furthermore, while wood is readily available in considerable quantity, bone material is an extremely limited resource that must be used in an extremely efficient manner.

Various types of bone grafts are known. For example, as disclosed in U.S. Pat. No. 5,989,289 to Coates et al., a spinal spacer includes a body formed of a bone composition such as cortical bone. The spacer has walls that define a chamber that is sized to receive an osteogenic composition to facilitate bone growth.

U.S. Pat. No. 5,899,939 to Boyce et al. discloses a bone-derived implant for load-supporting applications. The implant has one or more layers of fully mineralized or partially demineralized cortical bone and, optionally, one or more layers of some other material. The layers constituting the implant are assembled into a unitary structure, as by joining layers to each other in edge-to-edge fashion in a manner analogous to planking.

With a rapidly increasing demand in the medical profession for devices incorporating bone material, the tremendous need for the tissue material itself, particularly allograft tissue material, presents a considerable challenge to the industry that supplies the material. Due to the size and shape of the bones from which the material is harvested, and the dimensional limitations of any particular type of bone in terms of naturally occurring length and thickness (i.e. cortical or cancellous), there is a need for a means by which individual bone fragments can be combined to form larger, integral implants that are more suitable for use in areas of larger fractures or defects. For example, the size of cortical bone fragments needed to repair a fracture or defect site is often not available in a thick enough form. While multiple fragments may together meet the size and shape requirements, several prominent concerns have placed a practical limitation on the implementation of this concept. here is considerable uncertainty regarding the structural integrity provided by fragments positioned adjacent to one another without bonding or other means of securing the fragments to each other. Moreover, there is concern over the possibility that a fragment may slip out of position, resulting in migration of the fragment and possible further damage in or near the area of implantation.

In addition, due to the geometry of bones such as the femur and tibia, all portions of the bones are not readily usable as a result of size limitations. Thus, prior art implants, specifically allografts, are produced with an inefficient use of source bones.

There is a need for new approaches to working with and processing tissues, in particular allograft material, especially with regard to machining, mating, and assembling bone fragments. Specifically, there is a need for an implant that allows more efficient use of source material. More specifically, there is a need for an implant that is an integrated implant comprising two or more bone fragments that are interlocked to form a mechanically effective, strong unit.

Furthermore, there is a need for implants that may span the vacancy between two bony regions, such as for use in corpectomies, long bone reconstruction, tibial osteotomies, filling bony defects, and interbody fusions. There is also a need for skeletal reconstruction implants formed of bone and other materials that permit a wide range of angles, heights, and configurations to be accommodated so that a particular anatomical defect may be spanned.

SUMMARY OF THE INVENTION

The present invention is related to a corpectomy cage including a central body having first and second ends, a first end cap, and a second end cap. The first end cap is coupled to one end of the central body and the second end cap is coupled to the other end of the central body. The first end may be disposed in a first body plane and the second end may be disposed in a second body plane, the first and second planes converging with respect to each other. A first alignment plane extending perpendicular to the central axis is disposed at a first angle with respect to the first body plane, and a second alignment plane extending perpendicular to the central axis is disposed at a second angle with respect to the second body plane, with the first and second angles being about the same. The first and second angles may be between about 1° and about 3°. The end caps each include a top face disposed in a first cap plane and a bottom face disposed in a second cap plane, the first and second cap planes being disposed at a cap angle with respect to each other. The first angle, second angle, and cap angle may be about the same and between about 1° and about 3°. In some embodiments, one of the central body and an end cap has a protrusion and the other further has a recess, with the protrusion being configured and dimensioned for mating with the recess. The protrusion and recess may be non-circular, and if the protrusion is symmetrical about a central protrusion axis, the protrusion is selectably positionable within the recess in two orientations.

The central shaft may be threadably associated with at least one end cap, and each end cap may include a migration-resistant surface. Also, the central body may have a hole extending from the first end to the second end, with the hole disposed about a central axis. The skeletal reconstruction cage may further include a core configured and dimensioned to be received in the hole, with the core being formed of bone.

In some embodiments, the skeletal reconstruction cage includes a core, the central body includes a hole extending from the first end toward the second end with the hole disposed about a central axis, and at least one of the central body, first end cap, second end cap, and core is formed from bone. The core is configured and dimensioned to be received in the hole. At least one of the central body, first end cap, second end cap, and core may be formed of cancellous bone or cortical bone of autograft, allograft, or xenograft bone tissue and may be partially demineralized or demineralized bone tissue. At least two of the central body, first end cap, second end cap, and core may be fastened together with at least one fastener selected from a screw, key, pin, peg, rivet, cotter, nail, spike, bolt, stud, staple, boss, clamp, clip, dowel, stake, hook, anchor, tie, band, crimp, and wedge. At least two of the central body, first end cap, second end cap, and core may be bonded together with a bonding agent, and at least one may be at least partially dehydrated to fit against a surrounding mating surface or to mate with another component.

The present invention is also related to a method of providing variable fit for a skeletal reconstruction cage. The method includes: providing a first set of central bodies, each central body having a different maximum height from one another; providing a second set of top end caps of variable sizes, each top end cap having a different maximum height from one another; providing a third set of bottom end caps of variable sizes, each bottom end cap having a different maximum height from one another; selecting the central body, top end cap, and bottom end cap that provide preferred skeletal reconstruction cage height when coupled together; coupling the first and second end caps to the central body to form a first skeletal reconstruction cage, with the end caps disposed on opposing ends of the central body. The method may further include: providing a fourth set of inserts of variable sizes, each insert having a different maximum height from one another; selecting the insert that provides preferred height when disposed in a hole in the central body; and inserting the insert in the central body. At least one of the central body, top end cap, bottom end cap, and insert may be formed of bone.

In addition, the present invention is related to a skeletal reconstruction cage including a central body having first and second free ends, with each end including a receiving region. The cage also includes a first end cap coupled to one free end of the central body and having a first protruding region, and a second end cap coupled to the other free end of the central body and having a second protruding region. The first protruding region and the second protruding region are configured and dimensioned to be received in the receiving regions, and each of the regions is symmetrical about at least one central plane extending generally perpendicular to the first and second free ends. In some embodiments, at least one of the central body, first end cap, and second end cap is formed from bone.

Furthermore, the present invention is related to an end cap for use with a skeletal reconstruction cage. The end cap includes a cap body having a top face disposed in a first cap plane and a bottom face disposed in a second cap plane transverse to the first cap plane, with the first and second cap planes being disposed at a cap angle with respect to each other. The cap angle may be between about 1° and about 3°, and the cap body may be formed of bone.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1A:
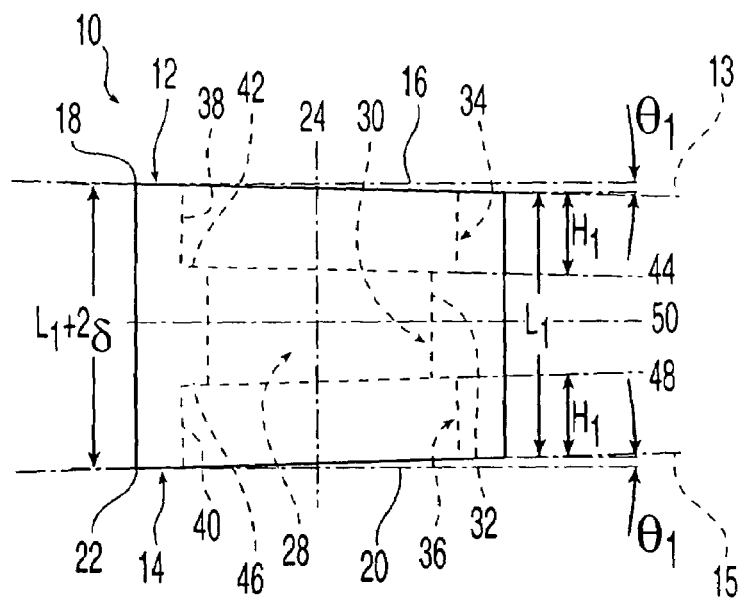
FIG. 1A shows a side view of a central shaft for use with a skeletal reconstruction cage of the present invention.

Any of a wide variety of different implant structures, particularly allograft, autograft, and/or xenograft implant structures, can be prepared according to the teachings of the present invention. While a representative selection of implant structures are described and depicted herein, additional disclosure is found in U.S. Provisional Application No. 60/191,099 filed Mar. 22, 2000, which is hereby incorporated herein in its entirety by reference, including all figures.

As used in the description of the present invention, the words fitting, interfitting, mating, locking, interlocking, meshing, and interlacing are all used generically to describe the joining of bone sections or pieces together. Thus, these words are not limited to the use of any particular manner of joining. Thus, for example, the press-fitting of one bone section within a cavity formed in another bone section may be described using any of the above-mentioned terms. In addition, although various preferred mechanical fastening approaches are described, the present invention allows the use of any mechanical device for joining two or more separate parts of an article or structure. Such mechanical devices include, but are not limited to the following: screws, keys, pins, pegs, rivets, cotters, nails, spikes, bolts, studs, staples, bosses, clamps, clips, dowels, stakes, hooks, anchors, ties, bands, and crimps. Also, bonding agents or other chemical means for joining two separate parts may be employed alone or in combination with the mechanical devices. Thus, as appropriate, the means disclosed herein for fixing bone sections to each other may be substituted, as with the above-mentioned mechanical devices, bonding devices, or chemical means. Furthermore, although particular types of joints are disclosed, the present invention is directed to the creation of implants that may be joined using other joints.

While the present invention is preferably directed to the creation of implants from allograft material, the present invention may also be applied to implants that utilize other materials, including but not limited to the following: xenograft, autograft, metals, alloys, ceramics, polymers, composites, and encapsulated fluids or gels. Furthermore, the implants described herein may be formed of materials with varying levels of porosity, such as by combined bone sections from different bones or different types of tissue having varying levels of porosity. For example, cancellous bone is available in a range of porosities based on the location in the body from which the bone is harvested. Extremely porous cancellous bone may be harvested from various areas such as the iliac crest, while less porous bone may be harvested from areas such as a tibial condyle. Thus, the materials properties—particularly the porosity—of the bone components may be selected to meet the needs of a given application.

Cancellous bone components may be attached to syringes or aspirators, and blood or other fluids such as bone-growth inducing substances may be drawn into the components. The use of mechanically applied pressure, such as with aspiration devices, permits a greater degree of fluid absorption and/or concentration to be achieved than otherwise readily obtainable by soaking bone in such fluids without applying pressure from a device. In embodiments of the present invention that include hollow regions, a component of cancellous bone formed using the aforementioned technique may be inserted therein.

Also, the implants described herein may be formed of bone materials with varying mineral content. For example, cancellous or cortical bone may be provided in natural, partially demineralized, or demineralized states. Demineralization is typically achieved with a variety of chemical processing techniques, including the use of an acid such as hydrochloric acid, chelating agents, electrolysis or other treatments. The demineralization treatment removes the minerals contained in the natural bone, leaving collagen fibers with bone growth factors including bone morphogenic protein (BMP). Variation in the mechanical properties of bone sections is obtainable through demineralization. Advantageously, use of a demineralizing agent on natural bone transforms the properties of the bone from a stiff structure to a relatively pliable structure when it is hydrated. Some portions of interfitting bone components may be demineralized in order to achieve improved interfitting. For example, a tissue form may include two bone components having portions that are coupled together with an interference fit. The interference fit may be enhanced if the surface region of one of the components is demineralized so that it is pliable and exhibits some elasticity and/or malleability.

In addition, while many of the embodiments described herein show bone components disposed at right angles, or joints formed with right angles, angles that are greater or less than ninety degrees may alternatively be used in implants of the present development. For example, implants are generally described herein for use in the spine with total angulations of less than about 10°. However, the cages of the present invention may also mate with defect faces at significantly greater angles. Long bone defects, breaks, or other vacancies formed by bone tissue removal, for example, may require cages that mate at angles between about 0° and about 90°. Tibial osteotomies and femoral voids may require larger cages than discussed herein, as well as different angulation. Similarly, other bony defects or interbody fusions may use cages of the general structure disclosed herein, but having different dimensional requirements. Other applications may include the use of cages in regions in which vertebral bodies have been partially removed.

The components that are used to create implants of the present invention may all be formed from cortical bone, all from cancellous bone, or a combination of components formed from cortical and cancellous bone. The interfitting of the components may be achieved through a variety of means, including but not limited to the following: pinning, bonding with a suitable bone bonding agent or chemical means, press fitting, threadably engaging (as by helically screwing one component into another), snap fitting, inserting a tapered component into a component with a matching inner surface, or other interlocking means such as will be described in other embodiments. Serrations, ribbing, scoring, or other undulating features may be used on edges or faces of bone components to provide positive interlocking or friction fits between components. While the present development preferably allows the creation of implants from all bone material, it is also anticipated that one or more components used to create the implants may be formed of non-bone material such as a synthetic or other material. Thus, while the implants disclosed herein are typically described as being formed primarily from bone, the implants alternatively may be formed in whole or in part from other materials such as hydroxyapatite, metal, resorbable material, polymer, and ceramic, and may additionally incorporate bone chips, bone particulate, bone fibers, bone growth materials, and bone cement. Also, while solid-walled structures are described herein, the structures optionally may include perforations extending from outer to inner surfaces, or recesses formed in outer surfaces that do not extend through inner surfaces. Geometries such as circular depressions, dimples formed from a spherical geometry, diamond shapes, or rectangular shapes may be used.

Bones suitable for forming implants of the present invention include a radius, humerus, tibia, femur, fibula, or ulna, although other bones may be used.

The moisture content of the bone sections also may be varied to advantageously permit improved interlocking. Bone sections initially may be provided with moisture content as follows: (1) bone in the natural state fresh out of the donor without freezing, (2) bone in the frozen state, typically at −40° C., with moisture content intact, (3) bone with moisture removed such as freeze-dried bone, and (4) bone in the hydrated state, such as when submersed in water. The expansion and contraction properties that can be obtained from bone during heating, cooling, dehydrating, and hydrating permit an alternate approach to achieving a tight press-fit. In addition, the use of such approaches can provide a tighter press-fit than otherwise obtainable, as well as decrease the manufacturing tolerances required for mating sections of bone.

Turning now to FIGS. 1 to 8, cages for use in spinal fusions are described. While cages for use in the thoracic and lumbar regions of the spine are shown and described, the cages of the present invention also may be used in the cervical region of the spine, as well as in other regions of the body such as the long bones, as discussed previously. Although the spinal cages disclosed herein are particularly suited to use in the spine for addressing corpectomies, the cages are referred to herein as skeletal reconstruction cages due to the potential use for the cages in other regions of the body.

Figure 1B:
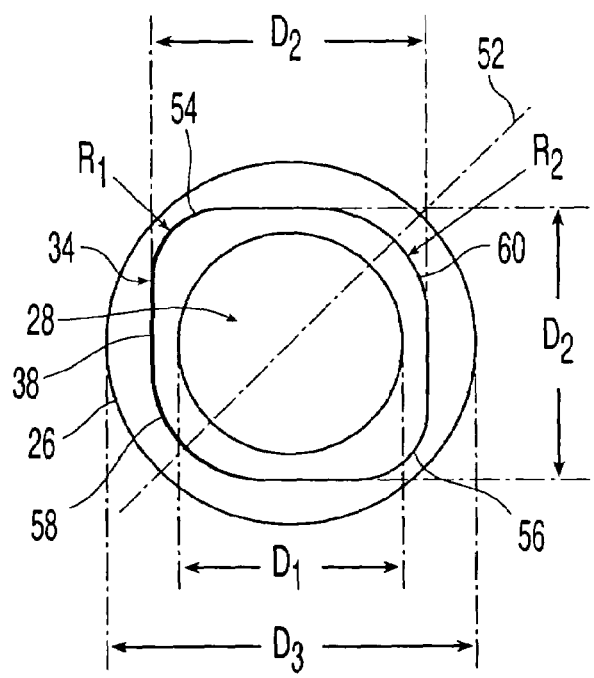
FIG. 1B shows a top view of the central shaft of FIG. 1A.

Referring to FIGS. 1–3, a skeletal reconstruction cage suitable for use in the thoracic region of the spine is shown. In a preferred embodiment, the skeletal reconstruction cage is formed from cortical bone. Turning to FIGS. 1A and 1B, a central shaft 10 includes a top face 12 and a bottom face 14, which preferably are nonparallel. In an alternate embodiment, faces 12, 14 may be generally parallel; angulation may be achieved by choosing suitable geometry for end caps that abut faces 12, 14. Top face 12 is disposed in a top plane 13 that is preferably sloped at an angle $\theta_1$ with respect to a horizontal plane 16 extending from the highest vertical point 18 of central shaft 10. Similarly, bottom face 14 is disposed in a plane 15 that is preferably sloped in converging orientation with respect to top face 12 at the same angle $\theta_1$ with respect to a horizontal plane 20 extending from the lowest vertical point 22 of central shaft 10. In alternate embodiments, top and bottom faces 12, 14, respectively, may be sloped at different angles. Preferably, angle $\theta_1$ is between about 1° and about 20°, and more preferably about 1.5°. However, vacancies resulting from removal of bone tissue due to cancer or vacancies resulting from deformities may require that significantly greater angulation be provided. With such an orientation of top and bottom faces 12, 14, respectively, central shaft 10 has a minimum longitudinal height $L_1$ and a maximum longitudinal height $L_1+2\delta$, the change in height from $L_1$ resulting from an increase in height of $\delta$ for each angle $\theta_1$.

Central shaft 10 is disposed about a central axis 24 and preferably has an outer surface 26 that is generally cylindrical. Alternatively, outer surface 26 may conform to the natural shape of a bone, or it may be a kidney shape, trapezoidal shape, or other geometry. A hole 28 extends from top face 12 to bottom face 14. Hole 28 includes a first portion 30 with a wall 32 that is generally parallel to outer surface 26 and defines a first inner diameter $D_1$ that is preferably between about 11 mm and 13 mm. Central shaft 10 may be formed, for example, from a humerus. Alternate embodiments with a central shaft 10 may be formed from the cross section of a bone; if the natural anatomical geometry of the bone canal and/or outer surface of the bone is preserved, wall 32 may not be parallel to outer surface 26. Second and third portions 34, 36 with walls 38, 40, respectively, define recesses into which end caps are placed, as will be described shortly. Wall 38 of second portion 34 is preferably perpendicular to top face 12, while shoulder 42 is preferably disposed in a plane 44 parallel to plane 13. Similarly, wall 40 of third portion 36 is preferably perpendicular to bottom face 14, while shoulder 46 is preferably disposed in a plane 48 parallel to plane 15. Alternate embodiments of central shaft 10 may not include shoulders 42, 46. Preferably, second and third portions 34, 36 are symmetrical about plane 50, which is disposed halfway between points 18, 22 and runs perpendicular to central axis 24.

Second portion 34 of central shaft 10 will now be described, although the foregoing description also applies to third portion 36. As can be seen in FIG. 1B, second portion 34 is symmetrical about line 52, and includes opposing arcuate regions 54, 56 each having a radius of curvature $R_1$, and opposing arcuate regions 58, 60 each having a radius of curvature $R_2$. Preferably, radius of curvature $R_1$ is between about 3.0 mm and about 4.0 mm, and more preferably about 3.5 mm, while radius of curvature $R_2$ is between about 5.0 mm and about 6.0 mm, and more preferably about 5.5 mm. Thus, second portion 34 is keyed such that a like-shaped portion of an end cap may be inserted therein in two orientations, as also will be described shortly. Second portion 34 is generally square, with wall 38 having a maximum separation $D_2$ that is preferably between about 12 mm and about 15 mm, and more preferably about 13.5 mm. Outer surface 26 of central shaft 10 preferably also has an outer diameter $D_3$ between about 17 mm and about 20 mm, and more preferably between about 18 mm and about 19 mm. Second and third portions 34, 36 each extend to a depth $H_1$ below top and bottom faces 12, 14, respectively, of between about 3 mm and about 5 mm, and more preferably about 4 mm.

Alternate embodiments of second and third portions 34, 36, respectively, may be round, square, diamond shaped, or star shaped, and preferably are symmetrical about at least one central axis. Shapes with symmetry about more than one central axis, such as a square that is symmetrical about two diagonal axes that extending through opposing pairs of corners, provide additional versatility.

Figure 2A:
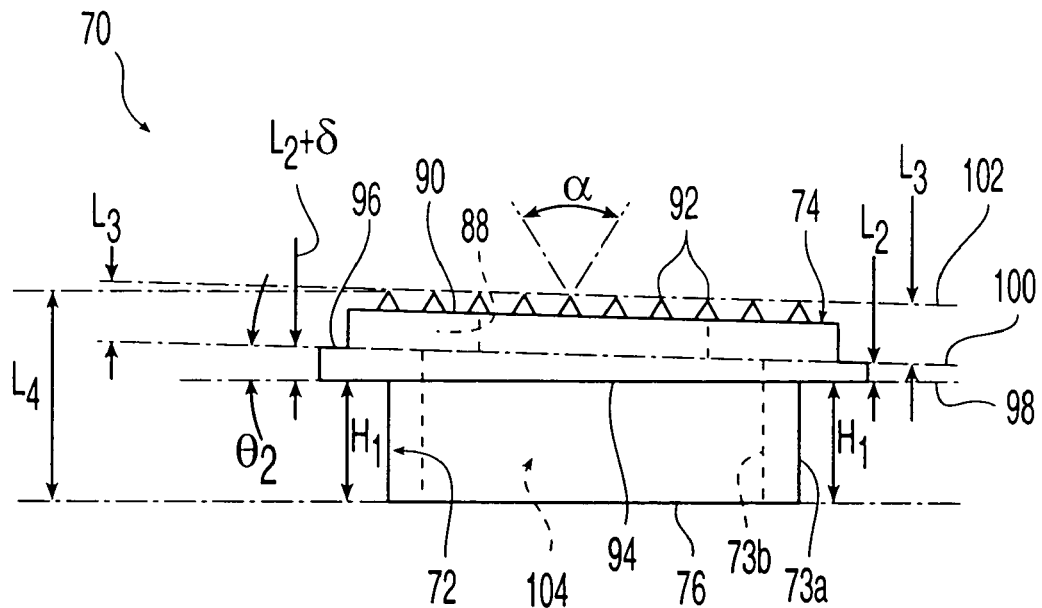
FIG. 2A shows a side view of an end cap of the present invention for use with the central shaft of FIG. 1A.
Figure 2B:
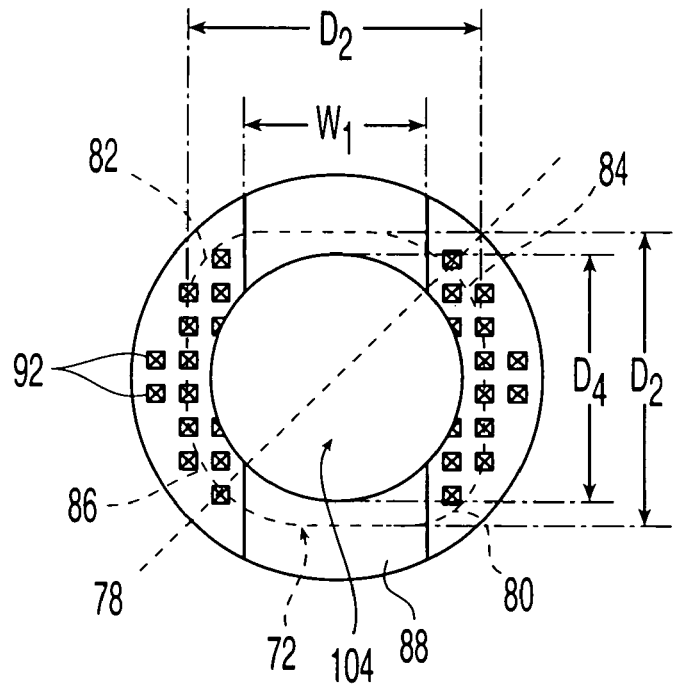
FIG. 2B shows a top view of the end cap of FIG. 2A.

Referring now to FIGS. 2A to 2B, an end cap 70 suitable for coupling to central shaft 10 is shown. End cap 70 includes a base portion 72 with an outer wall 73a and an inner wall 73b, and a ridge portion 74. Base portion 72 is sized to fit in a second or third portion 34, 36, with lower face 76 extending a distance of about $H_1$ so as to abut a shoulder 42, 46. Base portion 72 is symmetrical about line 78, and includes opposing arcuate regions 80, 82 each having a radius of curvature of about $R_1$, and opposing arcuate regions 84, 86 each having a radius of curvature of about $R_2$. Thus, when base portion 72 is inserted into a second or third portion 34, 36, each arcuate region 80, 82 will fit in a central shaft arcuate region 54, 56, while each arcuate region 84, 86 will fit in a central shaft arcuate region 58, 60. The remaining portions of outer wall 73a are generally square, as described with respect to second and third portions 34, 36. In an alternate embodiment, the remaining portions of outer wall 73a may be another geometry such as round. Thus, allowing for a slight variation in dimensions between base portion 72 and second and third portions 34, 36, a press-fit may be achieved between an end cap 70 and central shaft 10.

Ridge portion 74 of end cap 70 includes a slot 88; an implant having opposing end caps 70 with opposing slots 88 thus may be grasped by a surgeon using a suitable tool to facilitate placement of the implant in the body. Thus, slot 88 may be used to guide insertion of an implant under distraction. Preferably, slot 88 has a width $W_1$ of between about 7 mm and about 9 mm, and more preferably about 8 mm. Ridge portion 74 includes a first, upper face 90 with teeth 92, a second face 94, and a third face 96 formed by slot 88. Second and third faces 94, 96 are disposed in planes 98, 100, respectively, which are preferably sloped at an angle $\theta_2$ with respect to each other. Preferably, angle $\theta_2$ is about the same as angle $\theta_1$ as previously described with respect to central shaft 10. In an alternate embodiment, the angulations of second and third faces 94, 96 are different. In addition, teeth 92 preferably extend to a plane 102 that is parallel to plane 100 and separated by a distance $L_3$. Preferably, distance $L_3$ is between about 1.7 mm and 2.1 mm, and more preferably about 1.9 mm. There is a minimum distance $L_2$ between second and third faces 94, 96 and a maximum distance $L_2+\delta$.

Hole 104 extends from upper face 90 to lower face 76. Preferably, dimensions $D_1$, $D_4$ are about the same and between about 10 mm and 12 mm, and more preferably about 11 mm. In alternate embodiments, dimensions $D_1$, $D_4$ may be different from each other. As will be described with respect to an end cap 210, shown for example in FIG. 6B, upper face 90 of end cap 70 may be curvilinear such that teeth 92 are disposed along a curve rather than in a single plane as shown in FIG. 2A.

A variety of patterns and geometries of teeth 92 may be provided on end cap 70, and serve to resist migration of end cap 70 with respect to adjacent bony areas after implantation. In one embodiment, teeth 92 are pyramidal in shape, with opposing pyramidal edges disposed at an angle $\alpha$ with respect to each other. Preferably, angle $\alpha$ is between about 50° and about 70°, and more preferably about 60°. Alternatively, migration restricting structures such as saw teeth, regular teeth, spurs or grooving may be provided.

Figure 3A:
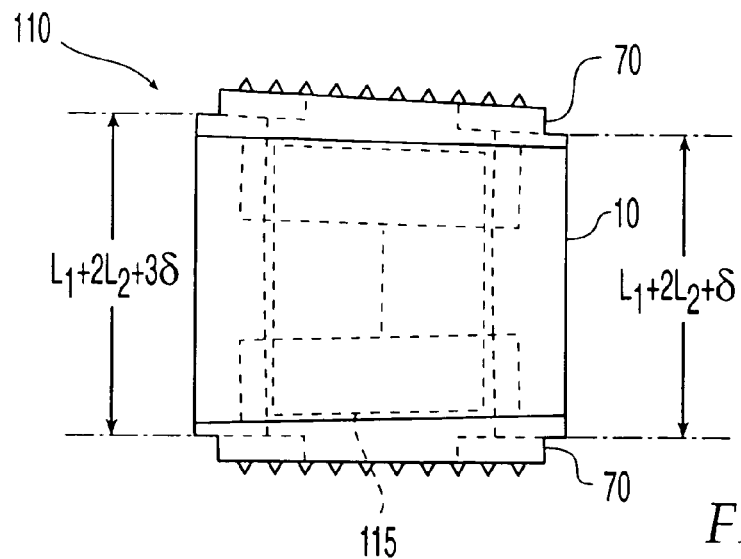
FIGS. 3A to 3C show side views of central shafts with a pair of end caps disposed thereon.
Figure 3B:
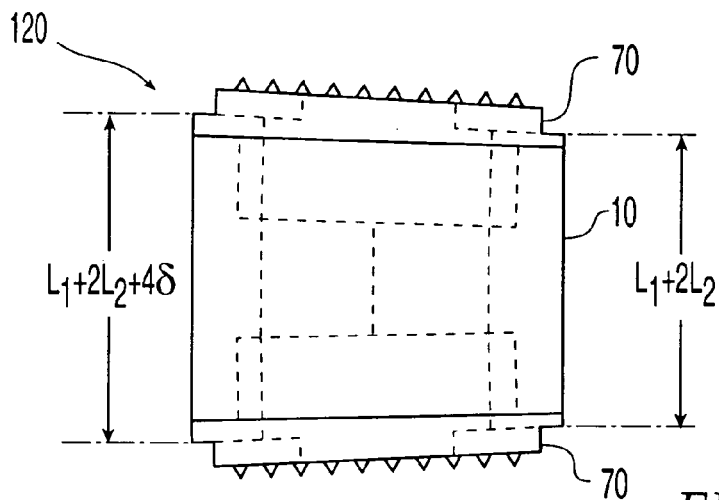
Figure 3C:
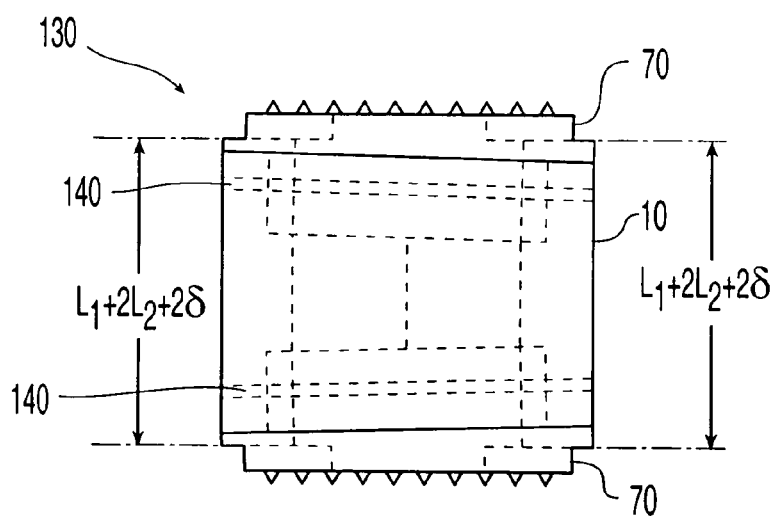

Turning now to FIGS. 3A to 3C, constructions of skeletal reconstruction cages using a central shaft 10 and a pair of end caps 70 are shown. As discussed earlier, top and bottom faces 12, 14, respectively, of central shaft 10 have a minimum longitudinal height $L_1$ and a maximum longitudinal height $L_1+2\delta$, with the change in height from $L_1$ resulting from an increase in height of $\delta$ for each angle $\theta_1$. Also, second and third faces 94, 96 of end cap 70 are preferably sloped at an angle $\theta_2$ with respect to each other, with angle $\theta_2$ being about the same as angle $\theta_1$. Thus, the end caps 70 may be disposed in such a manner that the following constructions of skeletal reconstruction cages 110, 120, 130 are obtained:

TABLE 1

| Skeletal Reconstruction Cage | Maximum Height | Minimum Height | Angulation of End Caps |
|---|---|---|---|
| 110 | $L_1 + 2L_2 + 3\delta$ | $L_1 + 2L_2 + \delta$ | 3° |
| 120 | $L_1 + 2L_2 + 4\delta$ | $L_1 + 2L_2$ | 6° |
| 130 | $L_1 + 2L_2 + 2\delta$ | $L_1 + 2L_2 + 2\delta$ | 0° |

Figure 3D:
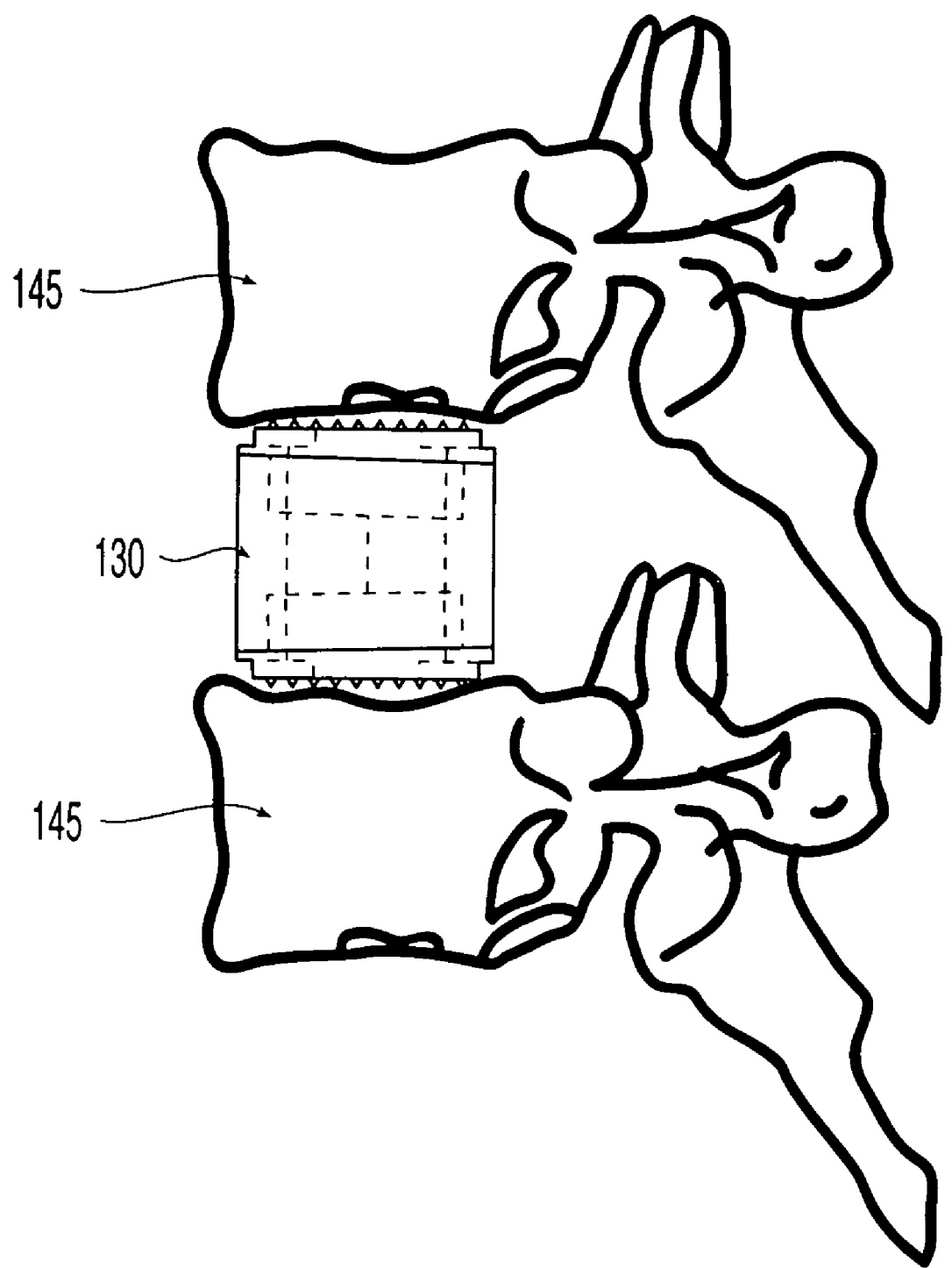
FIG. 3D shows a side view of a skeletal reconstruction cage disposed between a pair of vertebral bodies.

As listed in Table 1, the configurations of end caps 70 coupled to a central shaft 10 permit cap angulations of about 0°, 3°, and 60°, respectively, assuming that each distance $\delta$ results from a separation $\theta_1$ or $\theta_2$ of about 1.5°. For example, the angulation achieved by end caps 70 on skeletal reconstruction cage 110 is determined by taking the difference between the maximum height, $L_1+2L_2+3\delta$, and the minimum height, $L_1+2L_2+\delta$, which difference is $2\delta$ or about 30°. Referring to FIG. 3D, a skeletal reconstruction cage 130 is shown disposed between a pair of vertebral bodies 145.

In addition, central shafts 10 may be provided with various maximum overall heights $L_1+2\delta$ such as 14 mm, 24 mm, and 34 mm, and suitable minimum heights as required by the geometrical constraints described above. Similarly, end caps 70 may be provided with various overall maximum heights $L_4$ such as 3 mm, 5 mm, 7 mm, 9 mm, and 11 mm, and suitable minimum heights as required by the geometrical constraints described above. The present invention provides a means by which a significant number of construct heights can be created using a small number of different central shafts 10 and end caps 70. Thus, a kit of skeletal reconstruction cages may be created for use by a surgeon, for example, during corpectomy procedures. In particular, the kit may include a variety of sizes of central shafts 10 and end caps 70 so that for a given height of void to be spanned by a skeletal reconstruction cage, the surgeon may construct a suitable cage. For example, a kit may be created with central shaft 10 sizes of 14 mm, 24 mm, and 34 mm, as well as end cap 70 sizes of 3 mm, 5 mm, and 7 mm. A kit with these components permits a surgeon to construct skeletal reconstruction cages with overall maximum heights as listed in Table 2:

TABLE 2

| Shaft Height (mm) | First End Cap Height (mm) | Second End Cap Height (mm) | Overall Maximum Cage Height (mm) |
|---|---|---|---|
| 14 | 3 | 3 | 20 |
| 14 | 3 | 5 | 22 |
| 14 | 3 | 7 | 24 |
| 14 | 5 | 5 | 24 |
| 14 | 5 | 7 | 26 |
| 14 | 7 | 7 | 28 |
| 24 | 3 | 3 | 30 |
| 24 | 3 | 5 | 32 |
| 24 | 3 | 7 | 34 |
| 24 | 5 | 5 | 34 |
| 24 | 5 | 7 | 36 |
| 24 | 7 | 7 | 38 |
| 34 | 3 | 3 | 40 |
| 34 | 3 | 5 | 42 |
| 34 | 3 | 7 | 44 |
| 34 | 5 | 5 | 44 |
| 34 | 5 | 7 | 46 |
| 34 | 7 | 7 | 48 |

As shown by Table 2, a kit with six sizes of components permits a significant range in skeletal reconstruction cage heights (a 28 mm range is provided in Table 2). Notably, a kit with only one shaft for each of the three shaft heights and only two end caps for each of the three end cap heights would require a total of about 126 mm of bone, while a kit with unitary cages (i.e., manufactured as one piece) for each of the 15 heights in Table 2 would require about 612 mm of bone (assuming base portions on caps of about 4 mm each in length). Thus, a substantial savings is realized with a kit of the present invention. In addition, greater flexibility may be provided by providing a range of separations $\theta_1$ and/or $\theta_2$.

Figure 4A:
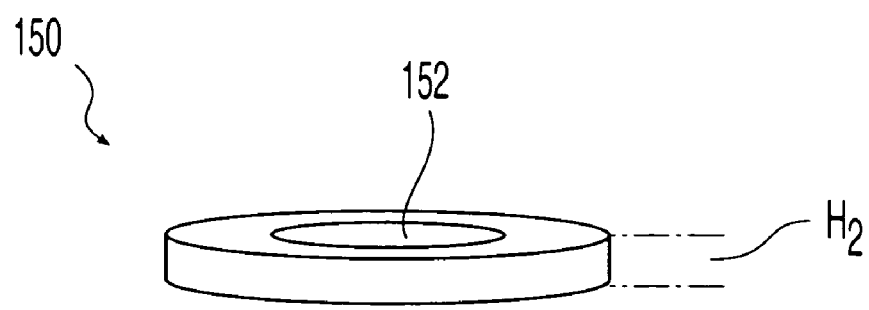
FIG. 4A shows a washer-like structure for use with a skeletal reconstruction cage of the present invention.
Figure 4B:
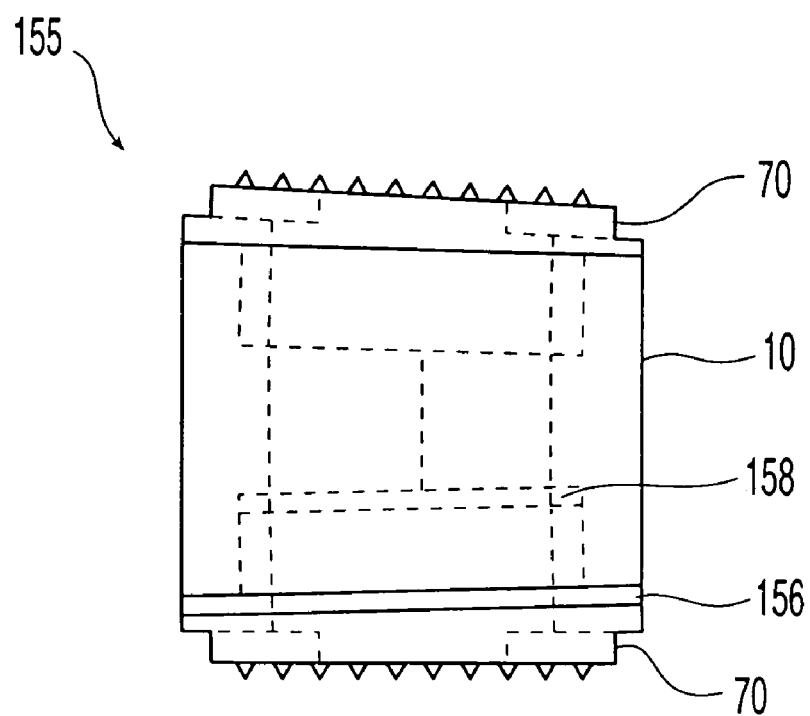
FIG. 4B shows a side view of a skeletal reconstruction cage that includes a pair of washer-like structures.

If height adjustment is desired at even smaller increments, washer-like structures 150 may be provided for mounting, for example, on base portions 72 of end caps 70, or alternatively within second or third portions 34, 36. As shown in FIG. 4A, structures 150 may be provided with heights $H_2$, preferably between about 1 mm and about 4 mm, as well as inner holes 152. Referring to FIG. 4B, skeletal reconstruction cage 155 includes a first washer-like structure 156 mounted on a base portion 72, and a second washer-like structure 158 disposed within a third portion 36. Preferably, structures 156, 158 have about the same heights.

Furthermore, although the embodiment of the present invention described above permits rotation of an end cap 70 by 180° with respect to a central shaft 10, alternate mating configurations may instead be used to permit other. rotations such as 90° (i.e., square mating configurations). Also, while the above-described end caps 70 and central shaft 10 each include two pairs of opposing arcuate surfaces with different radii, other geometries may also be used to limit rotation of an end cap 70 with respect to a central shaft 10. For example, rotation of 180° may be achieved using an elliptical or diamond shape. Such shapes. advantageously prevent undesired torsional rotation of an end cap 70 with respect to a central shaft 10, and facilitate proper assembly of a skeletal reconstruction cage by a surgeon.

End caps 70 may be offered with various configurations of slots suitable for different surgical approaches, including lordotic, anterior, anterolateral, and lateral. Multiple slots such as parallel slots may be provided, and the end caps may also have a variety of overall outer diameters, inner diameters, and edges such as radiused edges, chamfered edges, and flat edges. Depending on the size of cage that is required, the central shafts and end caps may be fabricated from a variety of bones including the femur, humerus, tibia, fibula, radius, or ulna.

End caps 70 and central shafts 10 may be secured to each other using a variety of techniques. Preferably, a press-fit is used between these components. Alternatively, or in addition, one or more pins, screws, or other mechanical securing elements may be used such as pins 140 shown in FIG. 3C. As discussed above, other suitable manners for securing the components include bonding agents or other chemical means. Alternate mechanical fasteners such as screws or keys, as described above, may be used. Other interfitting such as with interlocking features may be used as well, including ribbing, threading, tapers, knurled surfaces, interference lips in which a lip on one component fits in a groove in another component, flanges, or other joints. In addition, while skeletal reconstruction cages 110, 120, 130 are constructed with end caps 70 and central shafts 10 that have flat, mating surfaces, other types of joints may be employed to interfit these components including joints that permit articulation such as a ball and socket type of joint, and particularly joints that permit firm interlocking between two components to prevent relative movement between the components. Preferably, mortise and tenon joints can be used to interfit components of the skeletal reconstruction cages. Other coupling arrangements such as edge joints including tongue and groove joints, rabbeted joints, toothed joints, and dovetail joints are also suitable for the present invention.

Holes 28, 104 in skeletal reconstruction cages 110, 120, 130 may be packed with a variety of materials. For example, a cancellous plug may be inserted into holes 28, 104. Such a cancellous plug would serve to promote bone fusion, and could be highly concentrated or otherwise soaked with bone growth substances or blood prior to insertion. A greater degree of fluid absorption and/or concentration may be achieved using a syringe or aspirator to draw blood or other fluids through the plug. Other packing materials include bone chips, slurries of bone particulate, bone fibers, or bone-growth inducing substances.

Figure 5A:
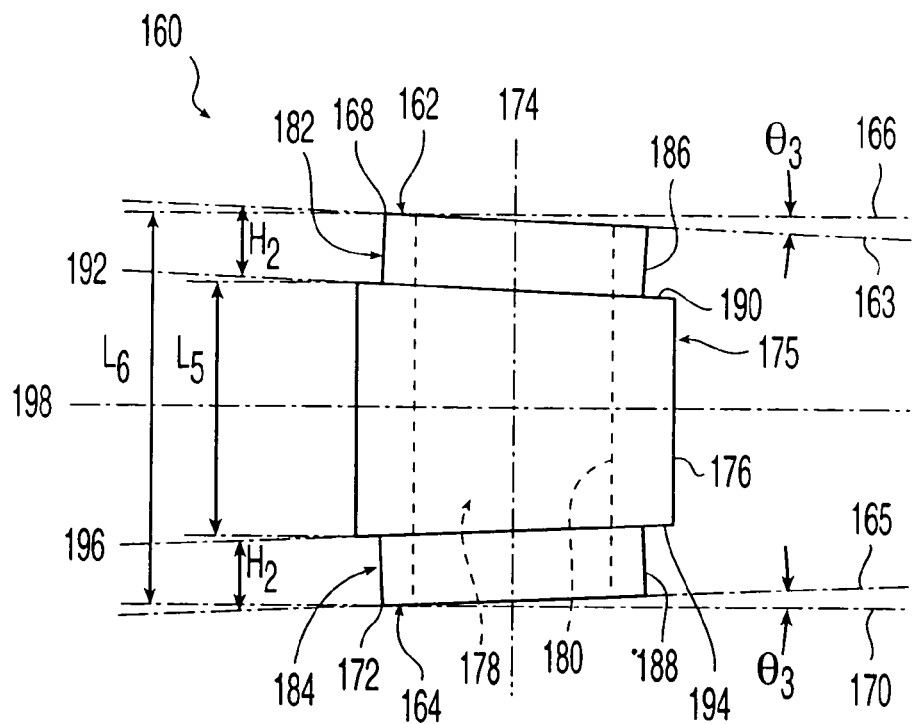
FIG. 5A shows a side view of another central shaft for use with a corpectomy cage of the present invention.
Figure 5B:
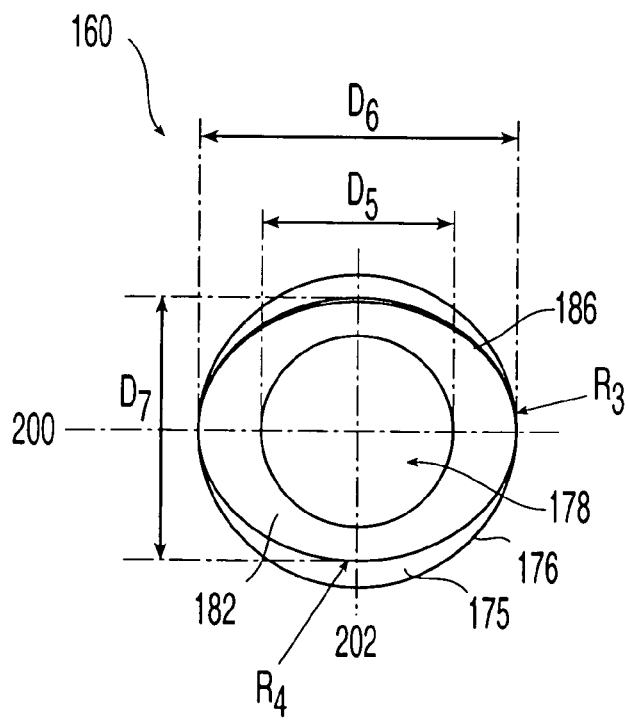
FIG. 5B shows a top view of the central shaft of FIG. 5A.

Referring to FIGS. 5 to 6, an embodiment of a skeletal reconstruction cage suitable for use in the lumbar region of the spine is shown. Turning to FIGS. 5A to 5B, a central shaft 160 includes a top face 162 and a bottom face 164, which preferably are nonparallel. Top face 162 is disposed in a top plane 163 that is preferably sloped at an angle $\theta_3$ with respect to a horizontal plane 166 extending from the highest vertical point 168 of central shaft 160. Similarly, bottom face 164 is disposed in a plane 165 that is preferably sloped in converging orientation with respect to top face 162 at the same angle $\theta_3$ with respect to a horizontal plane 170 extending from the lowest vertical point 172 of central shaft 160. Preferably, angle $\theta_3$ is between about 2° and about 3°, and more preferably about 2.5°. A wider range of angulations may be used to meet the needs of voids in bones such as long bones.

Central shaft 160 is disposed about a central axis 174 and preferably has a central portion 175 with an outer surface 176 that is generally cylindrical. A hole 178 extends from top face 162 to bottom face 164, perpendicular to planes 166, 170. Hole 178 has a wall 180 that is generally parallel to outer surface 176 and defines an inner diameter $D_5$ that is preferably between about 11 mm and 13 mm. As described above, the geometry of the natural bone canal and natural outer surface may be used, in which case wall 180 and outer surface 176 may not be parallel to each other. Central shaft 160 also includes upper and lower portions 182, 184, respectively, with outer walls 186, 188, and which define protrusions onto which end caps are placed, as will be described shortly. Wall 186 of upper portion 182 is preferably perpendicular to top face 162, while shoulder 190 is preferably disposed in a plane 192 parallel to plane 163. Similarly, wall 188 of lower portion 184 is preferably perpendicular to bottom face 164, while shoulder 194 is preferably disposed in a plane 196 parallel to plane 165. Preferably, upper and lower portions 182, 184 are symmetrical about plane 198, which is disposed halfway between points 168, 172 and runs perpendicular to central axis 174.

Upper portion 182 of central shaft 160 will now be described, although the foregoing description also applies to lower portion 184. Referring in particular to FIG. 5B, upper portion 182 is symmetrical about line 200. Preferably, upper portion 182 is generally elliptical, parabolic, or otherwise oblong with a major diameter $D_6$ along line 200 and a minor diameter $D_7$ along line 202. At the point at which wall 186 of upper portion 182 merges and becomes coplanar with wall 176 of central portion 175, the radius of curvature $R_3$ is about the same as the radius of curvature of circular wall 176, and preferably is between about 8 mm and 10 mm, and more preferably about 9 mm. Points on wall 186 of upper portion 182 at minor diameter $D_7$ on axis 202 have a radius of curvature $R_4$ preferably between about 6.5 mm and about 8.5 mm, and more preferably about 7.5 mm. Thus, upper portion 182 is keyed such that a like-shaped portion of an end cap may be inserted thereon in two orientations, as also will be described shortly. Circular wall 176 of central shaft 160 preferably also has an outer diameter $D_6$ between about 17 mm and about 20 mm, and more preferably between about 18 mm and about 19 mm. Upper and lower portions 182, 184 each have heights $H_2$ above and below planes 192, 196, respectively, of between about 3 mm and about 5 mm, and more preferably about 4 mm.

In one preferred embodiment, central portion 175 has a maximum length $L_5$ of between about 13.5 mm and about 15.5 mm, and more preferably about 14.5 mm. Other preferred lengths $L_5$ for central portion 175 are preferably between about 23.5 mm and about 25.5 mm, and more preferably about 24.5 mm, as well as between about 33.5 mm and about 35.5 mm, and more preferably about 34.5 mm. A set of three central portions may, for example, be provided with maximum heights $L_6$ of about 22.5 mm, 32.5 mm, and 42.5 mm.

As shown in FIGS. 6A to 6E, an end cap 210 suitable for coupling to central shaft 160 includes an outer wall 212, as well as a central hole disposed along axis 213 with a lower inner wall 214, an upper inner wall 216, and an inner ridge portion 218. Lower inner wall 214 extends about a depth $H_2$ and is sized to fit snugly on an upper or lower portion 182, 184 of central shaft 160 with an upper or lower face 162, 164 abutting a shoulder 218. Preferably, upper inner wall 216 has a dimension that is about the same as dimension $D_5$ of hole 178 of central shaft 160. End cap 210 is symmetrical about line 220, and is generally oblong in shape with first and second widths $W_2$, $W_3$. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160. Preferably, first width $W_2$ is between about 26 mm and about 34 mm, and more preferably about 30 mm, while second width $W_3$ is between about 20 mm and about 28 mm, and more preferably about 24 mm. Also, preferably first and second widths $W_2$, $W_3$ are within about 4 mm and about 8 mm of each other. In addition, preferably the sizing of central shaft 160 and end caps 210 allows for a slight variation in dimensions between lower inner wall 214 of end cap 210 and walls 186, 188 of upper and lower portions 182, 184, respectively, so that a press-fit may be achieved. Preferably, the wall thicknesses of end cap 210 are no smaller than about 4 mm. Heights A and B of end cap 210, shown in FIG. 6C, may be changed to provide different amounts of angulation.

End cap 210 includes a slot 222 for facilitating placement in the body. Preferably, slot 222 has a width $W_4$ of between about 8 mm and about 10 mm, and more preferably about 9 mm. End cap 210 also has an upper face 224 with teeth 226 to resist migration. Upper face 224 generally follows a curvilinear path and is convex, as shown for example in FIG. 6B. This geometry is useful in mating with the natural anatomical shape of a vertebral body, which is curved in the anterior-posterior plane.

Figure 6A:
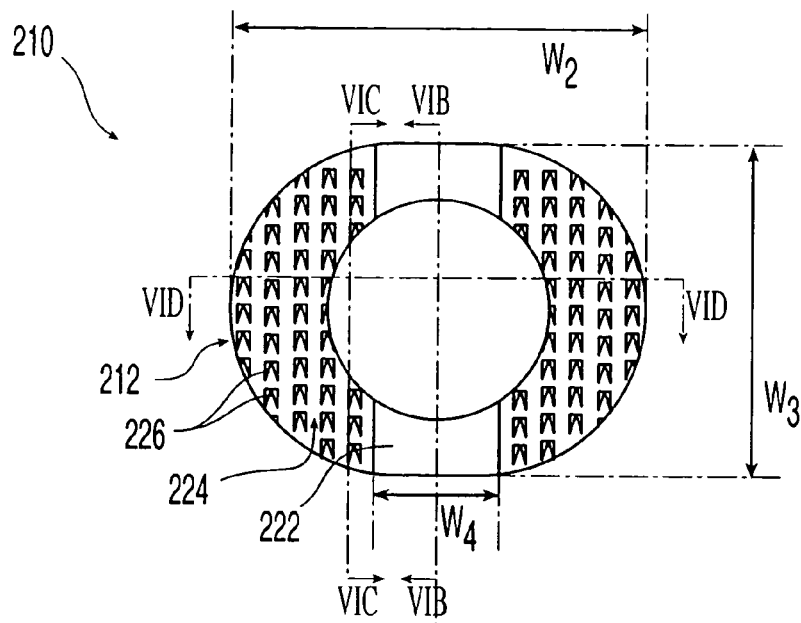
FIG. 6A shows a top view of an end cap of the present invention for use with the central shaft of FIG. 5A.
Figure 6B:
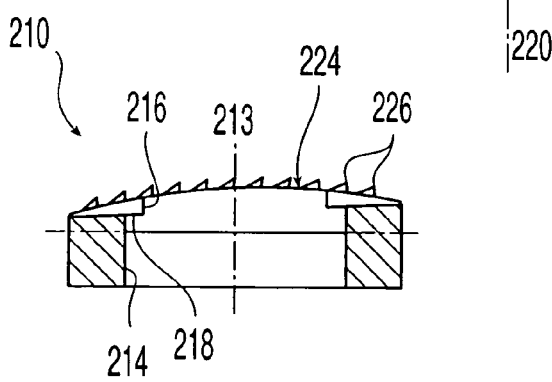
FIG. 6B shows a side, cross-sectional view of the end cap of FIG. 6A taken through line VIB—VIB.
Figure 6C:
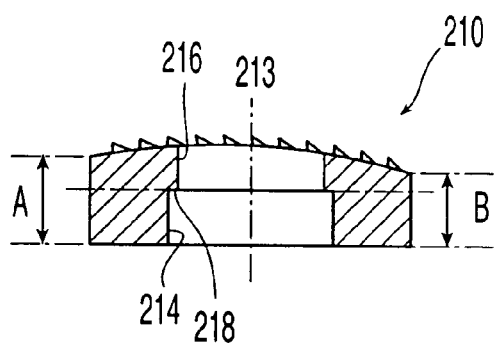
FIG. 6C shows a side, cross-sectional view of the end cap of FIG. 6A taken through line VIC—VIC.
Figure 6D:
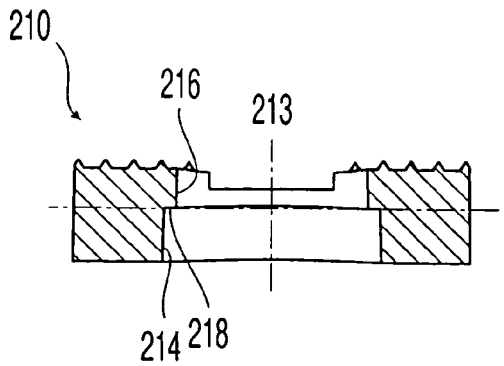
FIG. 6D shows a side, cross-sectional view of the end cap of FIG. 6A taken through line VID—VID.
Figure 6E:
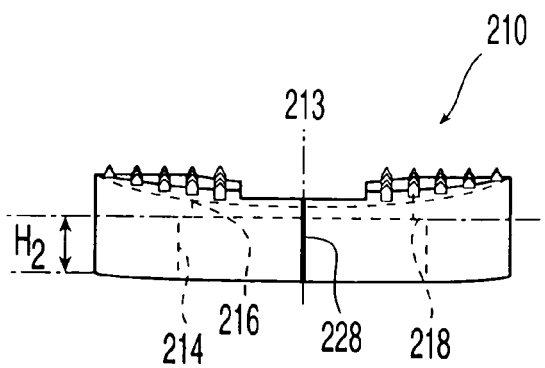
FIG. 6E shows a side view of the end cap of FIG. 6A.

Alignment indicia 228 such as a line along the side of end cap 210, as shown in FIG. 6E, may be provided on the outer surface of central shafts and/or end caps. Preferably, indicia 228 is an imprint, i.e. with ink, although indicia 228 may instead be provided in the form of surface scoring or a protrusion on the surface. Indicia 228 may serve to assist in properly orienting the components with respect to each other or with respect to particular anatomical features during insertion into an anatomical void. Indicia 228 also may be used to indicate the angulation of end cap 210. The indicia suitable for the present invention includes, but is not limited to, markers such as lines, arrows, lettering, and symbols.

Figure 6F:
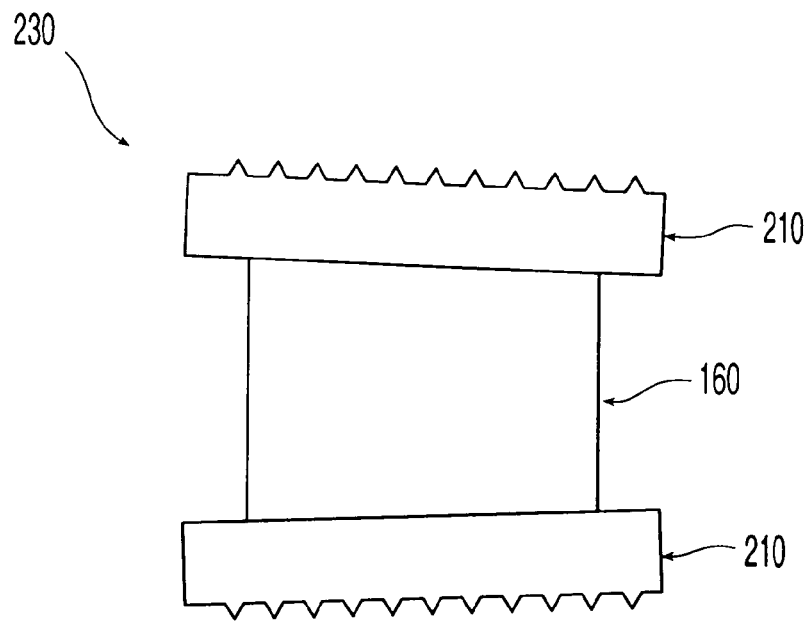
FIG. 6F shows a side view of a central shaft with a pair of end caps disposed thereon.
Figure 6G:
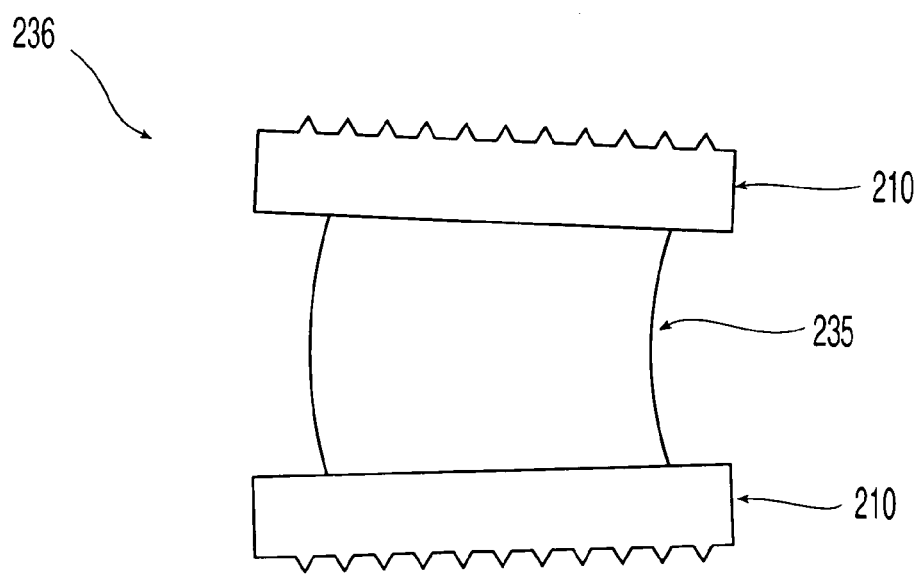
FIG. 6G shows a side view of a curved central shaft with a pair of end caps disposed thereon.

As shown in FIG. 6F, a generally I-shaped skeletal reconstruction cage 230 may thus be formed using a pair of end caps 210 disposed on central shaft 160. An alternative arcuate body 235 may be used with a pair of end caps 210 to form a cage 236, as shown in FIG. 6G. Body 235 is provided with curvature so that body 235 provides angulation for end caps 210.

Referring to FIGS. 7A–7E, another alternate embodiment of an end cap for coupling to a central body such as central shaft 160 is shown. End cap 240 includes an outer wall 242, as well as a central hole 243 disposed along axis 244 with a lower inner wall 245, an upper inner wall 246, and an inner ridge portion 248. Lower inner wall 245 extends about a depth $H_3$ and is sized to fit snugly on an upper or lower portion 182, 184 of central shaft 160 with an upper or lower face 162, 164 abutting a shoulder 248. Preferably, upper inner wall 246 has a diameter that is about the same as diameter $D_5$ of hole 178 of central shaft 160. End cap 240 is symmetrical about line 250, and is generally oblong in shape with first and second widths $W_5$, $W_6$. Notably, while outer wall 176 of central shaft 160 is generally circular, outer wall 242 of end cap 240 is generally oblong, so that a generally I-shaped skeletal reconstruction cage may be formed when a pair of end caps 240 are placed on central shaft 160. Preferably, first width $W_5$ is between about 26 mm and about 34 mm, and more preferably about 30 mm, while second width $W_6$ is between about 20 mm and about 28 mm, and more preferably about 24 mm. In addition, preferably the sizing of central shaft 160 and end caps 240 allows for a slight variation in dimensions between lower inner wall 245 of end cap 240 and walls 186, 188 of upper and lower portions 182, 184, respectively, of central shaft 160 so that a press-fit may be achieved. Thus, the dimensions of lower inner wall 245 are such that major and minor diameters $D_6$, $D_7$ of central shaft 160 are about the same as widths $W_7$, $W_8$, respectively, of end cap 240. Central hole 243 may have about the same diameter $D_8$ as diameter $D_5$ of hole 178 of central shaft 160, although the diameter may be smaller or larger to fit a particular need. In one embodiment, end cap 240 has a maximum height $L_7$ of between about 12 mm and about 14 mm, and preferably about 13 mm.

Figure 7A:
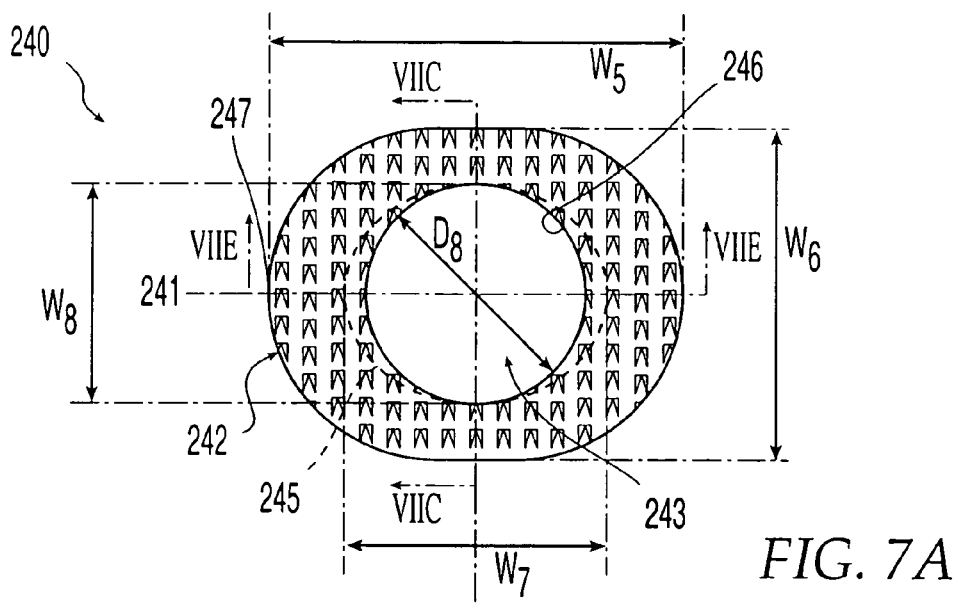
FIG. 7A shows a top view of another end cap of the present invention.
Figure 7B:
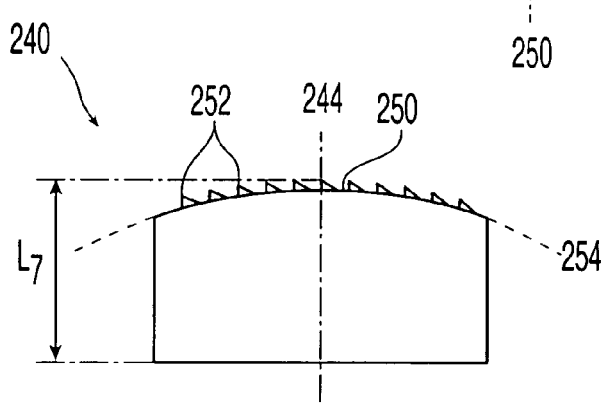
FIG. 7B shows a side view of the end cap of FIG. 7A.
Figure 7C:
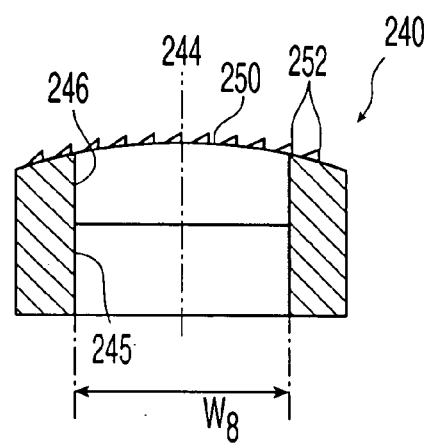
FIG. 7C shows a side, cross-sectional view of the end cap of FIG. 7A taken through line VIIC—VIIC.
Figure 7D:
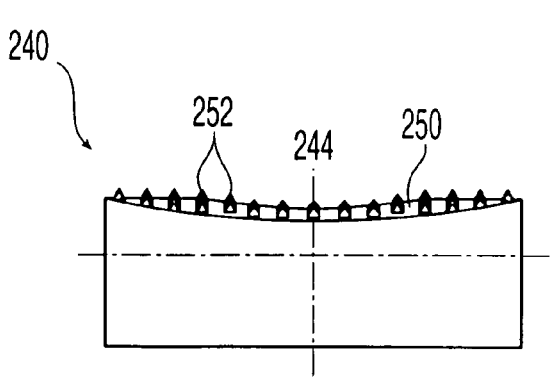
FIG. 7D shows another side view of the end cap of FIG. 7A.
Figure 7E:
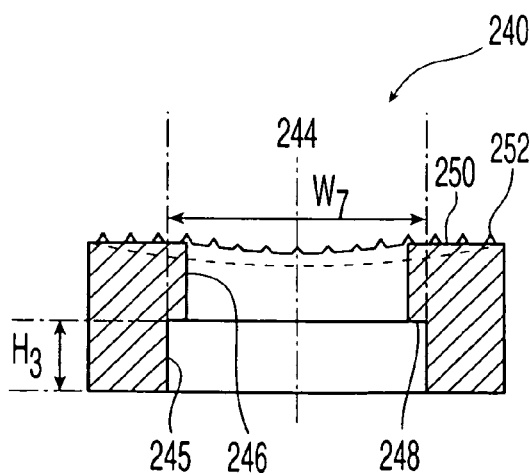
FIG. 7E shows a side, cross-sectional view of the end cap of FIG. 7A taken through line VIIE—VIIE.

End cap 240 also has an upper face 250 with teeth 252 to resist migration. Upper face 250 is generally convex, as shown for example in FIG. 7B along line 254, and thus may positively engage surrounding, concave anatomical tissue with similar geometry. The side view of FIG. 7B is taken along line 241, proximate the point 247 at which line 241 and end cap 240 intersect. Another side view taken along line 250 is shown in FIG. 7D.

Although press-fitting of end caps 240 on central shaft 160 has been described, other interfitting such as with interlocking features and joints described above may be used.

Figure 8A:
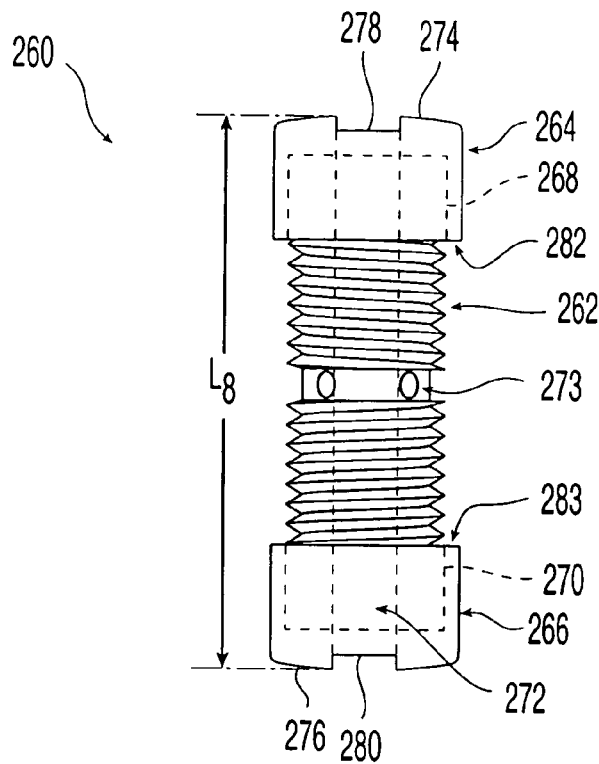
FIGS. 8A and 8B show additional embodiments of skeletal reconstruction cages of the present invention.

Another embodiment of a skeletal reconstruction cage 260 is shown in FIG. 8A. A threaded central strut 262 is provided with end caps 264, 266 that are threadably associated with central strut 262. End caps 264, 266 have threaded bores 268, 270, respectively, which threadably receive central strut 262. Preferably, right-handed threading is provided on central strut 262 proximate one of ends 274, 276, while left-handed threading is provided proximate the other end. The threading on end caps 264, 266 corresponds to the type of threading at a given location on central strut 262. Thus, the overall length $L_8$ of skeletal reconstruction cage 260 may be changed by screwing action of central strut 262 without rotational movement of end caps 264, 266. To aid in turning central strut 262 with respect to end caps 264, 266, a through-hole 273 is provided for insertion of a rod or other suitable device. A through-hole 272 extends from one free end 274 to the other free end 276, and may be packed with such materials as bone chips or a cancellous insert, as previously described. Notches 278, 280 may be provided on free ends 274, 276, respectively, to facilitate handling of the device by a surgeon. For added structural integrity, washer-like structures similar to previously described washer-like structures 150 may be provided for mounting about central strut 262 between end caps 264, 266 to fill the gap therebetween and provide a skeletal reconstruction cage with a uniform outer surface.

Figure 8B:
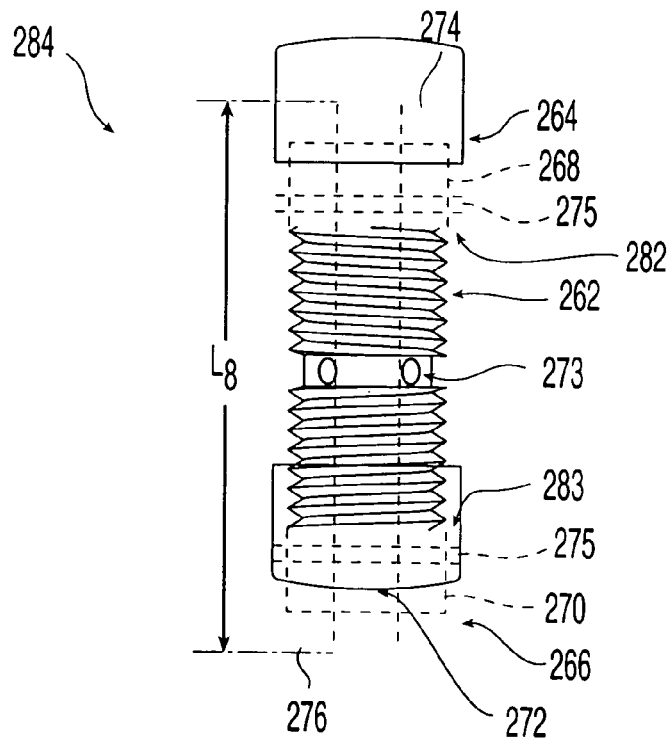

In an alternate embodiment, shown in FIG. 8B, skeletal reconstruction cage 284 is provided with end caps 264, 266 without slots 278, 280. In addition, pins 275 are provided to secure end caps 264, 266 to central strut 262 after a desired separation $L_8$ has been set. Once suitable distraction has been achieved, holes may be drilled in end caps 264, 266 for the insertion of pins 275 to maintain the desired distraction height. Alternatively, caps 264, 266 may be provided with pre-drilled holes through which subsequent drilling is conducted for pin insertion. In addition, set screws may be used to lock central strut 262 in place. In some embodiments, end caps 264, 266 may be provided with angled or convex free ends 274, 276, respectively. Other features may be provided such as tapering, threading, and ribbing, as described previously with respect to other embodiments.

Figure 8C:
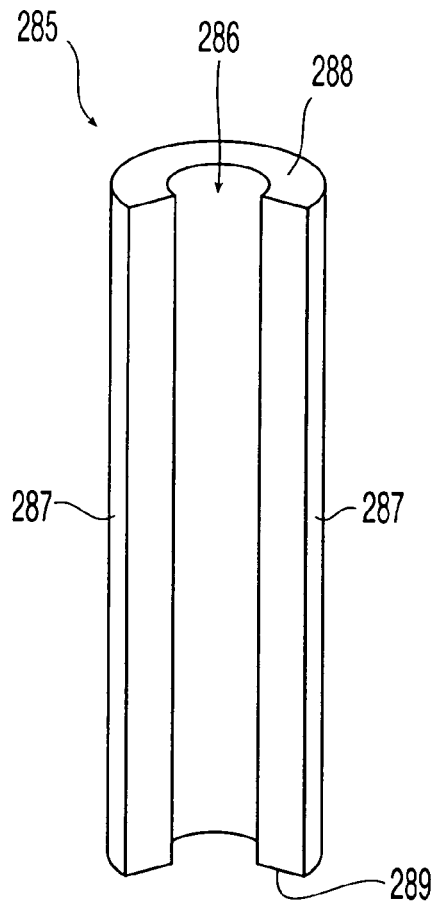
FIG. 8C shows a generally C-shaped support member for use with the skeletal reconstruction cages of FIGS. 8A and 8B.

Once suitable separation is achieved between end caps 264, 266 of cages 260, 284, a support member 285, as shown in FIG. 8C, may be inserted between end caps 264, 266 to further support the end caps. Preferably, support 285 is generally C-shaped, with a central arcuate groove 286 that may generally conform to the outer diameter of central strut 262. Outer surface 287 preferably is sized with about the same outer diameter as end caps 264, 266. The C-shape of support 285 facilitates coupling to central strut 262, and in particular, arcuate groove 286 preferably spans a circular arc of more than 180° so that support 285 may be flexed during installation but clamps to central strut 262 to resist removal. Faces 288, 289 abut faces 282, 283 of end caps 264, 266, respectively. In order to achieve a proper fit, a support 285 may be cut so that it has the desired height. Also, support member 285 may be fixed to end caps 264, 266 and/or central strut 262, such as with one or more suitable fasteners.

Figure 9:
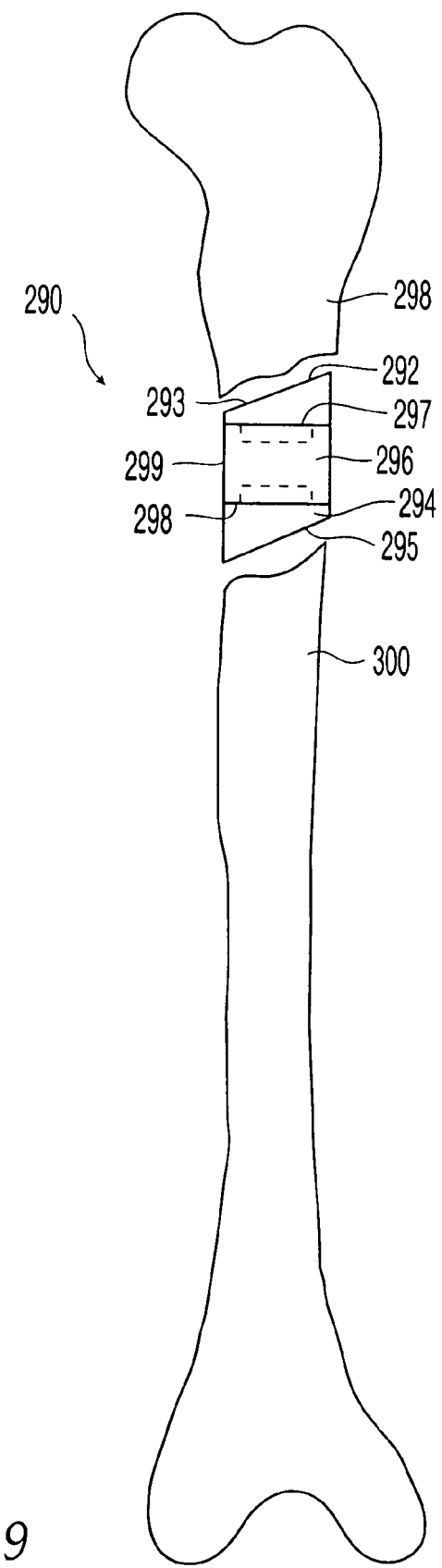
FIG. 9 shows a partial exploded side view of a long bone with an additional skeletal reconstruction cage of the present invention disposed therein.

As shown in FIG. 9, a skeletal reconstruction cage 290 formed according to the present invention includes pair of end caps 292, 294 with a body 296 disposed therebetween. Faces 293, 295 of end caps 292, 294, respectively, are generally parallel to each other, forming a cage 290 in the shape of a parallelogram in cross-section, and are preferably disposed at an angle of between about 30° and about 60° with respect to a plane parallel to body free ends 297, 298. The free ends 297, 298 are disposed in planes that are generally parallel to each other and generally perpendicular to cylindrical outer surface 299. Cage 290 spans the vacancy between bone sections 298, 300, which may for example be a vacancy in the femur.

The implants contemplated by the present invention may be made of allograft, autograft, or xenograft bone material as well, or combinations of autograft, allograft, and xenograft bone material. In addition, the implants may also be formed from cancellous bone, cortical bone, or combinations thereof and the choice of such materials may be based on the materials properties obtainable from a given type of bone. As discussed earlier, cancellous bone is available in a range of porosities based on the location in the body from which the bone is harvested. While extremely porous cancellous bone may be harvested from various areas such as the iliac crest, less porous bone may be harvested from areas such as a tibial condyle. Thus, the materials properties—particularly the porosity—of the implants may be selected to meet the needs of a given application. In addition, the implants of the present invention may be formed either partially or completely using non-bone materials such as metals, alloys, ceramics, polymers, composites, and encapsulated fluids or gels.

Figure 10A:
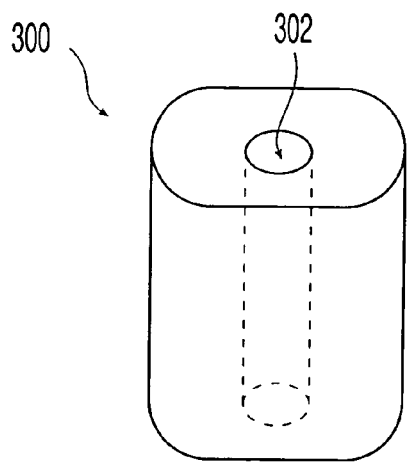
FIGS. 10A to 10D show inserts formed according to the present invention for use with skeletal reconstruction cages.
Figure 10B:
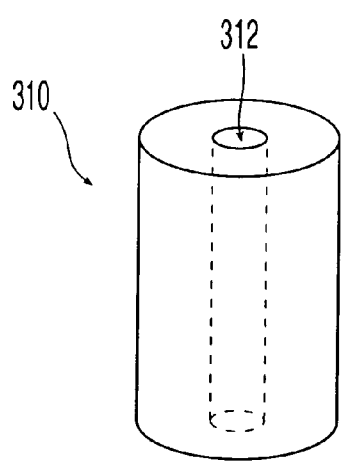
Figure 10C:
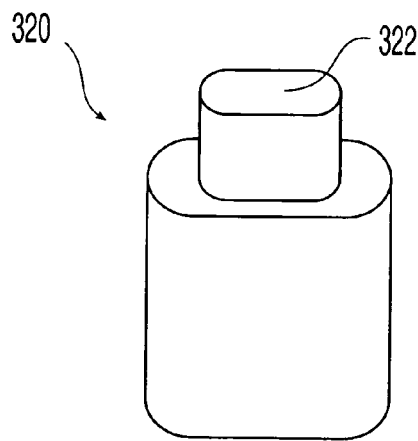
Figure 10D:
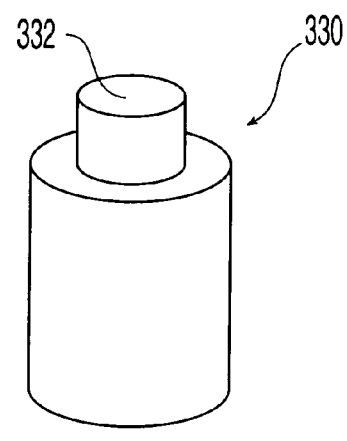
Figure 10E:
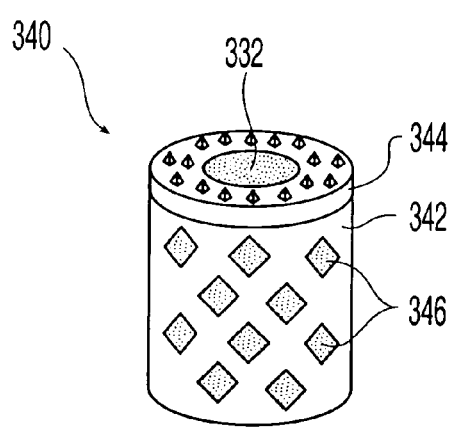
FIG. 10E shows a skeletal reconstruction cage with an insert retained therein according to the present invention.
Figure 10F:
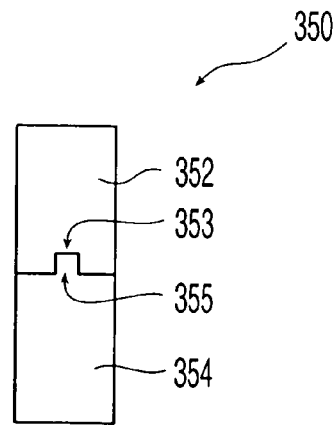
FIGS. 10F to 10H show additional inserts formed according to the present invention for use with skeletal reconstruction cages.
Figure 10G:
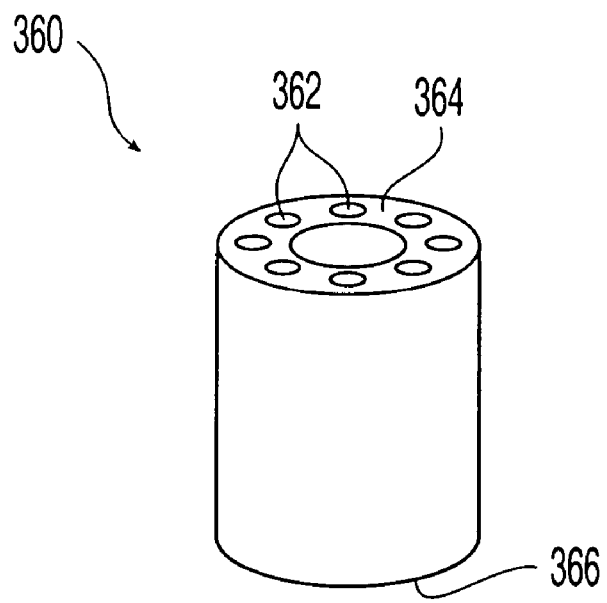
Figure 10H:
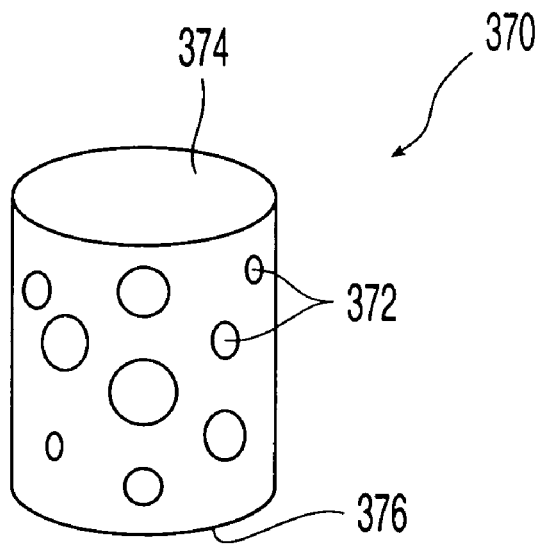

Turning to FIGS. 10A to 10H, a variety of pre-formed cancellous inserts may be used as an osteoconductive filler with cages such as those described herein. Preferably, the cancellous bone is harvested from any of the long bone condyles. One or more inserts may be used with a cage to meet the proper height requirements, for example, to substantially fill the cage. Cage 300 is oblong in shape, while cage 310 is round. Each cage 300, 310 may include a recessed region or through-hole region 302, 312, respectively. Preferably, regions 302, 312 are packed with osteoinductive materials. Additional configurations of cancellous inserts are shown in FIGS. 10C and 10D. Inserts 320, 330 include protruding portions 322, 332, respectively, which are sized to receive a cap. For example, as shown in FIG. 10E, a skeletal reconstruction cage 340 includes a sleeve 342 with a insert 330 disposed therein. A cap 344 is press-fit to protrusion 332. Perforations 346 extend through the wall of sleeve 342, exposing portions of cancellous insert 330 to surrounding anatomy when inserted in a bony region. Inserts such as those of FIGS. 10A to 10D may be interfitted to permit greater insert lengths to be formed. For example, as shown in FIG. 10F, a composite insert 350 is formed of two inserts 352, 354; insert 352 includes a female portion 353, while insert 354 includes a male portion 355. Female and male portions 353, 355 are sized to mate, and may be formed, for example, in a groove and tongue configuration or a central recess and central protrusion configuration. The joints, fastening components, and other securing means previously discussed also may be used. The inserts may be fashioned with through-holes for receiving osteoinductive substances. As shown in FIGS. 10G and 10H, inserts 360 and 370 include through-holes of varying sizes and orientations. Through holes 362 in insert 360 extend from free end 364 to free end 366, while through-holes 372 of insert 370 extend generally transverse to free ends 374, 376. In addition, each of ends 364, 366 and 374, 376 may be angulated, for example to accommodate lordosis. Through-holes 362, 372 may be filled with osteoinductive materials.

The pre-formed inserts of the present invention also are particularly suitable for use in skeletal reconstruction cages such as those formed from titanium mesh indicated for reinforcement of bony regions in orthopedic procedures and typically available in pre-formed round and oval-shaped cylinders. Preferably, sets of cancellous inserts are available for use with skeletal reconstruction cages. In one embodiment, oblong inserts are available with minor and major diameters, respectively, of: about 14.6 mm and about 19.6 mm, about 19.6 mm and about 25.6 mm, and about 23.6 mm and about 30.6 mm. Round inserts may be available with outer diameters of 7.6 mm, 9.6 mm, and 12.6 mm. The cancellous inserts may be provided in combination with cortical bone, which may in some embodiments be integrally formed therewith. In addition, some embodiments of the cancellous inserts may be demineralized or partially demineralized. Alternative materials for the inserts described herein include metals, alloys, ceramics, polymers, composites, and encapsulated fluids or gels. Cage 340 may be a metallic mesh which receives a suitably sized cancellous insert, such as the above-mentioned sizes.

Additional embodiments contemplated by the present invention include skeletal reconstruction cages formed of non-symmetrical bone sections, or non-symmetrical components such as different sized end caps.

The embodiments of skeletal reconstruction cages disclosed herein may include components that are initially provided with a first moisture content, but then allowed to assume a new configuration with a second moisture content. For example, in the embodiment shown in FIG. 3A, end cap 70 initially may be supplied with a first outer diameter and a first inner diameter. Subsequent freeze-drying of end cap 70 results in shrinkage such that end cap 70 assumes a configuration with a second outer diameter that is smaller than the first outer diameter, while having a second inner diameter that is smaller than the first inner diameter. When end cap 70 is rehydrated or treated with a swelling agent, end cap 70 may reassume a configuration with the first outer diameter and first inner diameter. By providing a bone section such as an end cap 70 in the freeze-dried state while at least partially disposed inside another bone section such as a central shaft 10 that may be loosely interference fit, rehydration of end cap 70 in place permits a tighter interference fit to be achieved. Notably, a bone section with no inner diameter may shrink in outer diameter only when freeze-dried. Thus, similarly, an insert to be disposed centrally in the hole in central shaft 10 may be the bone section that is rehydrated to provide a tighter mating and interference fit with central shaft 10. Use of these properties can permit greater variation in dimensional tolerance between bone sections during manufacture, while tight final assembly can still be achieved. In addition, protrusions on bone sections become smaller when dehydrated, but expand when rehydrated; in contrast, recesses in bone sections become smaller when hydrated, but larger when dehydrated. Temperature changes may also be used to achieve better interference fits.

The use of insertable securing elements such as keys, pegs, pins, wedges, or other suitable components in joints to assist in securing bone components such as end caps 70 and central shafts 10 to each other is also an effective approach to providing a stable joint. Keys, for example, may be inserted in notched or grooved areas in skeletal reconstruction cage components, serving as the securing element between two or more components. Parameters that may be varied when using insertable securing elements, such as keys, include the angle of application, the spacing of the elements, and the thicknesses of the elements.

While various descriptions of the present invention are described above, it should be understood that the various features can be used singly or in any combination thereof. The various types of joints and connections can be used on skeletal reconstruction cages of different sizes or configurations, such that the invention is not to be limited to only the specifically preferred embodiments depicted in the drawings.

Further, it should be understood that variations and modifications within the spirit and scope of the invention may occur to those skilled in the art to which the invention pertains. For example, multiple, differently shaped and sized skeletal reconstruction cages can be constructed to serve the desired purpose. Accordingly, all expedient modifications readily attainable by one versed in the art from the disclosure set forth herein are within the scope and spirit of the present invention and are to be included as further embodiments. The scope of the present invention is accordingly defined as set forth in the appended claims.

What is claimed is:

1. A method of providing variable fit for a skeletal reconstruction cage, the method comprising:

providing a first set of central bodies, each central body having a different maximum height from one another;

providing a second set of top end caps of variable sizes, each top end cap having a different maximum height from one another;

providing a third set of bottom end caps of variable sizes, each bottom end cap having a different maximum height from one another;

selecting the central body, top end cap, and bottom end cap that provide preferred skeletal reconstruction cage height when coupled together, with at least one of the central body, top end cap, and bottom end cap being formed of bone;

coupling the first and second end caps to the central body to form a first skeletal reconstruction cage, with the end caps disposed on opposing ends of the central body;

wherein the combination of the maximum height of the selected top end cap and the selected bottom end cap is greater than 15% of the maximum height of the selected central body.

2. The method of claim 1, further comprising:

providing a fourth set of inserts of variable sizes, each insert having a different maximum height from one another;

selecting the insert that provides preferred height when disposed in a hole in the central body;

inserting the insert in the central body.

3. The method of claim 2, wherein at least one of the selected top end cap, bottom end cap, and insert are formed of bone.

4. The method of claim 1, wherein the top end cap and bottom end cap are selected so that the skeletal reconstruction cage is symmetrical with respect to a central axis of the selected central body.

5. The method of claim 1, wherein the top end cap and bottom end cap are selected so that the skeletal reconstruction cage is asymmetrical with respect to a central axis of the selected central body.

6. The method of claim 1, further comprising: securing at least one of the selected end caps to the central body with a fastener.

7. The method of claim 1, further comprising: securing at least one of the selected end caps to the central body with a pin.

8. The method of claim 1, wherein the caps are coupled to the central body so that end faces of the caps are disposed in transverse planes.

9. The method of claim 1, wherein the caps are coupled to the central body so that end faces of the caps are angled at about 3° with respect to each other.

10. The method of claim 1, wherein the caps are coupled to the central body so that end faces of the caps are angled at about 6° with respect to each other.

11. A method of providing variable fit for a skeletal reconstruction cage, the method comprising:

providing a first set of central bodies, each central body having a different maximum height from one another;

providing a second set of top end caps of variable sizes, each top end cap having a different maximum height from one another;

providing a third set of bottom end caps of variable sizes, each bottom end cap having a different maximum height from one another;

providing a fourth set of inserts of variable sizes, each insert having a different maximum height from one another;

selecting the central body, top end cap, and bottom end cap that provide preferred skeletal reconstruction cage height when coupled together, with at least one of the central body, top end cap, and bottom end cap being formed of bone;

selecting the insert that provides preferred height when disposed in a hole in the central body;

inserting the insert in the central body; and coupling the first and second end caps to the central body to form a first skeletal reconstruction cage, with the end caps disposed on opposing ends of the central body.

12. The method of claim 11, wherein at least one insert is formed of bone.

13. The method of claim 11, wherein the top end cap and bottom end cap are selected so that the skeletal reconstruction cage is symmetrical with respect to a central axis of the selected central body.

14. The method of claim 11, wherein the top end cap and bottom end cap are selected so that the skeletal reconstruction cage is asymmetrical with respect to a central axis of the selected central body.

15. The method of claim 11, further comprising: securing at least one of the selected end caps to the central body with a fastener.

16. The method of claim 11, further comprising: securing at least one of the selected end caps to the central body with a pin.

17. The method of claim 11, wherein the caps are coupled to the central body so that end faces of the caps are disposed in transverse planes.

18. The method of claim 11, wherein the caps are coupled to the central body so that end faces of the caps are angled at about 3° with respect to each other.

19. The method of claim 11, wherein the caps are coupled to the central body so that end faces of the caps are angled at about 6° with respect to each other.

20. A method of providing variable fit for a skeletal reconstruction cage, the method comprising:

providing a first set of central bodies, each central body having a different maximum height from one another;

providing a second set of top end caps of variable sizes, each top end cap having a different maximum height from one another;

providing a third set of bottom end caps of variable sizes, each bottom end cap having a different maximum height from one another;

selecting the central body, top end cap, and bottom end cap that provide preferred skeletal reconstruction cage height when coupled together, with at least one of the central body, top end cap, and bottom end cap being formed of bone;

coupling the first and second end caps to the central body to form a first skeletal reconstruction cage, with the end caps disposed on opposing ends of the central body;

wherein the top end cap and bottom end cap are selected so that the skeletal reconstruction cage is asymmetrical with respect to a central axis of the selected central body.

21. The method of claim 20, further comprising: securing at least one of the selected end caps to the central body with a fastener.

22. The method of claim 20, further comprising: securing at least one of the selected end caps to the central body with a pin.

23. The method of claim 20, wherein the caps are coupled to the central body so that end faces of the caps are angled at about 3° with respect to each other.

24. The method of claim 20, wherein the caps are coupled to the central body so that end faces of the caps are angled at about 6° with respect to each other.

25. A method of providing variable fit for a skeletal reconstruction cage, the method comprising:

providing a first set of central bodies, each central body having a different maximum height from one another;

providing a second set of top end caps of variable sizes, each top end cap having a different maximum height from one another;

providing a third set of bottom end caps of variable sizes, each bottom end cap having a different maximum height from one another;

selecting the central body, top end cap, and bottom end cap that provide preferred skeletal reconstruction cage height when coupled together, with at least one of the central body, top end cap, and bottom end cap being formed of bone;

coupling the first and second end caps to the central body to form a first skeletal reconstruction cage, with the end caps disposed on opposing ends of the central body;

wherein the central body is substantially without apertures.

* * * * *